(12) United States Patent
Bartolucci et al.

(10) Patent No.: US 11,267,644 B2
(45) Date of Patent: Mar. 8, 2022

(54) AEROSOL FOAM DISPENSER AND METHODS FOR DELIVERING A TEXTURED FOAM PRODUCT

(71) Applicant: The Procter & Gamble Company, Cincinnati, OH (US)

(72) Inventors: Stefano Bartolucci, Singapore (SG); Douglas Charles Cook, South Lebanon, OH (US); Kenneth Shun Qiang Ang, Singapore (SG); Sarah Elizabeth Mullen, Cincinnati, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 265 days.

(21) Appl. No.: 16/666,879

(22) Filed: Oct. 29, 2019

(65) Prior Publication Data

US 2020/0148459 A1    May 14, 2020

Related U.S. Application Data

(60) Provisional application No. 62/757,416, filed on Nov. 8, 2018.

(51) Int. Cl.
*B65D 83/20* (2006.01)
*B65D 83/30* (2006.01)
*B65D 83/22* (2006.01)

(52) U.S. Cl.
CPC .......... *B65D 83/206* (2013.01); *B65D 83/30* (2013.01); *B65D 83/22* (2013.01)

(58) Field of Classification Search
CPC . B05B 7/0018; B05B 1/14; B65D 83/14–267; B65D 83/201; B65D 83/206; B65D 83/22; B65D 83/30; B65D 83/32; B65D 83/44

USPC ....... 222/402.13, 270, 402.21; 239/337, 343, 239/601
See application file for complete search history.

(56) References Cited

U.S. PATENT DOCUMENTS

| | | | |
|---|---|---|---|
| 2,430,718 A | 11/1947 | Jacobson | |
| 2,829,874 A * | 4/1958 | Freeman | A62C 3/0207 239/433 |
| 2,911,159 A | 11/1959 | Doyle | |
| 3,024,787 A * | 3/1962 | Birch | A61M 13/00 128/200.23 |

(Continued)

FOREIGN PATENT DOCUMENTS

| CN | 200977495 Y | 11/2007 |
|---|---|---|
| CN | 101863350 A | 10/2010 |

(Continued)

OTHER PUBLICATIONS

U.S. Appl. No. 16/194,502, filed Nov. 19, 2018, Bartolucci et al.

(Continued)

*Primary Examiner* — Paul R Durand
*Assistant Examiner* — Michael J. Melaragno
(74) *Attorney, Agent, or Firm* — John G. Powell; Alexandra S. Anoff

(57) ABSTRACT

A method of dispensing a textured foam from an aerosol container. The aerosol foam dispenser has a pressurizable outer container and an actuator. The actuator has a nozzle surface with one or more shaping orifices. The method can have a shape factor index from about 0.11 to about 1.

19 Claims, 13 Drawing Sheets

(56) References Cited

U.S. PATENT DOCUMENTS

| | | | |
|---|---|---|---|
| 3,032,803 A * | 5/1962 | Walshauser | B65D 83/285 |
| | | | 401/190 |
| 3,085,329 A * | 4/1963 | Golczynski | E01H 1/1213 |
| | | | 30/123.3 |
| 3,104,785 A | 9/1963 | Knapp | |
| 3,235,135 A | 2/1966 | Henri | |
| 3,247,640 A | 4/1966 | De Wayne Miles et al. | |
| 3,250,444 A | 5/1966 | Ward | |
| 3,333,744 A * | 8/1967 | Nilsen | B65D 83/14 |
| | | | 222/402.13 |
| 3,361,301 A | 1/1968 | Philip | |
| 3,415,426 A * | 12/1968 | Kleveland | B65D 83/34 |
| | | | 222/402.11 |
| 3,506,165 A | 4/1970 | Beard | |
| 3,584,789 A | 6/1971 | Traynor | |
| 3,672,546 A * | 6/1972 | Ruhle | B65D 83/30 |
| | | | 222/402.12 |
| 3,981,419 A | 9/1976 | Nilson | |
| 4,122,845 A | 10/1978 | Stouffer et al. | |
| D267,855 S | 2/1983 | French | |
| 4,433,797 A | 2/1984 | Galia | |
| 4,562,942 A | 1/1986 | Diamond | |
| 4,592,743 A | 6/1986 | Hjertman et al. | |
| 4,694,975 A | 9/1987 | Hagan | |
| 4,720,046 A * | 1/1988 | Morane | B65D 83/30 |
| | | | 239/343 |
| 4,796,812 A * | 1/1989 | Grollier | A61K 8/046 |
| | | | 239/303 |
| 4,877,156 A | 10/1989 | Clanet | |
| 4,892,232 A | 1/1990 | Martin | |
| 4,896,832 A | 1/1990 | Howlett | |
| 4,919,312 A | 4/1990 | Beard | |
| 4,941,598 A | 7/1990 | Lambelet, Jr. et al. | |
| 4,958,755 A * | 9/1990 | Gerstung | B65D 83/46 |
| | | | 222/402.23 |
| 5,031,802 A | 7/1991 | Joulia | |
| 5,056,690 A | 10/1991 | Ichihara | |
| D324,171 S * | 2/1992 | Morane | D9/688 |
| 5,105,995 A | 4/1992 | Martin | |
| 5,199,616 A | 4/1993 | Martin | |
| 5,305,930 A | 4/1994 | De Laforcade | |
| 5,368,231 A * | 11/1994 | Brunerie | B65D 83/14 |
| | | | 222/190 |
| 5,370,313 A | 12/1994 | Beard | |
| 5,429,280 A | 7/1995 | Bauer et al. | |
| 5,441,181 A | 8/1995 | Scheindel | |
| D364,811 S * | 12/1995 | Zimmerhackel | D9/448 |
| 5,520,310 A | 5/1996 | Bauer et al. | |
| 5,577,641 A | 11/1996 | De Laforcade | |
| 5,624,055 A | 4/1997 | Clanet | |
| 5,678,765 A * | 10/1997 | Dobbs | B05B 11/0005 |
| | | | 239/333 |
| 5,702,058 A * | 12/1997 | Dobbs | B05B 11/0005 |
| | | | 239/343 |
| 5,725,155 A * | 3/1998 | Grunenberg | B05B 7/0062 |
| | | | 239/343 |
| 5,730,332 A * | 3/1998 | Zimmerhackel | B05B 7/0068 |
| | | | 222/148 |
| 5,848,729 A * | 12/1998 | Thornton | B65D 83/682 |
| | | | 222/190 |
| D406,240 S * | 3/1999 | Guillemot | D9/448 |
| 5,875,927 A | 3/1999 | D'Andrade | |
| 5,904,274 A | 5/1999 | Warby | |
| 5,914,085 A | 6/1999 | Zimmerhackel | |
| 6,004,300 A | 12/1999 | Butcher | |
| 6,095,182 A | 8/2000 | Warby | |
| 6,260,738 B1 | 7/2001 | Kerr | |
| 6,334,553 B1 | 1/2002 | Bouras | |
| 6,405,898 B1 | 6/2002 | O'Connor et al. | |
| 6,607,106 B2 * | 8/2003 | Henry | B65D 83/30 |
| | | | 222/402.1 |
| 6,745,920 B2 | 6/2004 | Gupta | |
| 7,104,424 B2 | 9/2006 | Koianus | |
| 7,306,123 B2 | 12/2007 | Masuda | |
| 7,306,124 B2 | 12/2007 | Masuda | |
| 7,665,923 B2 | 2/2010 | Py et al. | |
| 8,006,868 B2 | 8/2011 | Geiberger et al. | |
| 8,191,802 B2 * | 6/2012 | Khan | B65D 83/20 |
| | | | 239/565 |
| 8,387,827 B2 | 3/2013 | Helf | |
| 8,616,417 B2 | 12/2013 | Neuhaus | |
| 8,720,747 B2 | 5/2014 | Hoagland | |
| 8,794,600 B2 * | 8/2014 | Chou | B01F 5/0496 |
| | | | 261/28 |
| 8,814,005 B2 * | 8/2014 | Banks | B05B 11/3087 |
| | | | 222/190 |
| 8,863,994 B2 | 10/2014 | Neuhaus et al. | |
| 8,950,691 B2 * | 2/2015 | Chen | B01F 3/04446 |
| | | | 239/393 |
| 9,211,994 B2 | 12/2015 | Andersen | |
| 9,403,636 B2 | 8/2016 | Bodet et al. | |
| 9,469,468 B2 | 10/2016 | Shibata | |
| 10,022,740 B2 | 7/2018 | Van Swieten et al. | |
| 10,227,173 B2 * | 3/2019 | Clauwaert | B65D 83/757 |
| 10,364,092 B2 | 7/2019 | Schroer et al. | |
| 10,364,093 B2 | 7/2019 | Bartolucci | |
| 10,370,178 B2 | 8/2019 | Schroer et al. | |
| 10,449,131 B2 | 10/2019 | Li et al. | |
| 10,479,587 B2 | 11/2019 | Mizoguchi et al. | |
| 10,625,929 B2 | 4/2020 | Bartolucci | |
| 10,625,930 B2 * | 4/2020 | Takahashi | B65D 83/68 |
| 10,717,094 B2 * | 7/2020 | Takagi | B05B 1/02 |
| 10,850,914 B2 | 12/2020 | Bartolucci | |
| 2002/0162450 A1 | 11/2002 | Frost | |
| 2005/0103811 A1 | 5/2005 | Heukamp | |
| 2006/0065677 A1 | 3/2006 | Py | |
| 2006/0196889 A1 | 9/2006 | Masuda | |
| 2006/0219823 A1 * | 10/2006 | Eberhardt | B65D 83/206 |
| | | | 239/590 |
| 2007/0051754 A1 | 3/2007 | Strand | |
| 2007/0090133 A1 | 4/2007 | Macleod et al. | |
| 2007/0095853 A1 | 5/2007 | Bonney et al. | |
| 2007/0125799 A1 | 6/2007 | Bonney | |
| 2007/0137643 A1 | 6/2007 | Bonney | |
| 2007/0164049 A1 | 7/2007 | Bonney | |
| 2007/0175917 A1 | 8/2007 | Bonney | |
| 2008/0061083 A1 | 3/2008 | Masuda | |
| 2008/0083776 A1 | 4/2008 | Gupta | |
| 2008/0149098 A1 | 6/2008 | Bonney | |
| 2008/0272144 A1 | 11/2008 | Bonney | |
| 2009/0050650 A1 * | 2/2009 | Walters | B65D 83/22 |
| | | | 222/153.11 |
| 2009/0272765 A1 | 11/2009 | Seki et al. | |
| 2010/0308082 A1 | 12/2010 | Lamble | |
| 2011/0011889 A1 | 1/2011 | Bonney | |
| 2012/0006859 A1 | 1/2012 | Wilkinson | |
| 2013/0019802 A1 | 1/2013 | Leck | |
| 2013/0068119 A1 * | 3/2013 | Kennedy | A45D 40/08 |
| | | | 101/364 |
| 2014/0209633 A1 | 7/2014 | Mcdaniel | |
| 2015/0090736 A1 * | 4/2015 | Erickson | B65D 83/206 |
| | | | 222/153.1 |
| 2016/0129197 A1 | 5/2016 | Hetting | |
| 2016/0302624 A1 * | 10/2016 | Little | B65D 83/48 |
| 2017/0182699 A1 | 6/2017 | Kase | |
| 2018/0072485 A1 | 3/2018 | Fore | |
| 2018/0201434 A1 | 7/2018 | Presche | |
| 2018/0243763 A1 * | 8/2018 | Eurippini | B65D 83/28 |
| 2018/0273280 A1 | 9/2018 | Bartolucci | B65D 83/7535 |
| 2018/0273290 A1 | 9/2018 | Claeys | |
| 2019/0030551 A1 * | 1/2019 | Williams | A62C 31/12 |
| 2019/0071242 A1 | 3/2019 | Bartolucci | |
| 2019/0152684 A1 | 5/2019 | Bartolucci | |
| 2020/0016045 A1 * | 1/2020 | Aubert | A61K 8/0241 |
| 2020/0016046 A1 * | 1/2020 | Aubert | A61K 8/25 |
| 2020/0108003 A1 | 4/2020 | Iwata et al. | |
| 2020/0148458 A1 * | 5/2020 | Bartolucci | B65D 83/44 |

(56) References Cited

U.S. PATENT DOCUMENTS

| | | |
|---|---|---|
| 2020/0316629 A1 | 10/2020 | Bartolucci |
| 2021/0039876 A1 | 2/2021 | Bartolucci et al. |

FOREIGN PATENT DOCUMENTS

| | | | |
|---|---|---|---|
| DE | 3147004 | A1 | 5/1983 |
| DE | 19937554 | A1 | 3/2001 |
| DE | 202016101580 | U1 | 8/2017 |
| EP | 0571280 | B1 | 5/1997 |
| EP | 1380520 | A2 | 1/2004 |
| EP | 3409618 | A1 | 12/2018 |
| FR | 1454371 | A | 9/1966 |
| FR | 2311593 | A1 | 12/1976 |
| FR | 2990421 | B1 | 2/2015 |
| GB | 1414637 | A | 11/1975 |
| JP | H0220959 | U | 2/1990 |
| JP | H0462677 | U | 5/1992 |
| JP | H0535772 | U | 5/1993 |
| JP | H066278 | U | 1/1994 |
| JP | 2000309387 | A | 11/2000 |
| JP | 2007532181 | A | 11/2007 |
| JP | 2009082814 | A | 4/2009 |
| JP | 2011067362 | A | 4/2011 |
| JP | 2018058591 | A | 4/2018 |
| WO | 9427890 | A1 | 12/1994 |
| WO | 2004045778 | A1 | 6/2004 |
| WO | 2017115827 | A1 | 7/2017 |

OTHER PUBLICATIONS

U.S. Appl. No. 16/184,367, filed Nov. 8, 2019, Bartolucci et al.
15395 PCT Search Report and Written Opinion for PCT/US2019/060172 dated Apr. 23, 2020.
All Office Actions, U.S. Appl. No. 16/907,677.
All Office Actions, U.S. Appl. No. 17/076,907.
All final and non-final office actions for U.S. Appl. No. 15/926,075.
All final and non-final office actions for U.S. Appl. No. 16/118,663.
All final and non-final office actions for U.S. Appl. No. 16/184,367.
All final and non-final office actions for U.S. Appl. No. 16/194,502.
European Search Report for 17162178.2 dated Aug. 21, 2017.
European Search Report for EP 17175852.7 dated Sep. 19, 2017.
European Search Report for EP 17189053.6 dated Feb. 28, 2018.
European Search Report for EP 17203315.1 dated May 4, 2018.
PCT International Search Report and Written Opinion for PCT/US2018/058653 dated Jan. 25, 2019.

* cited by examiner

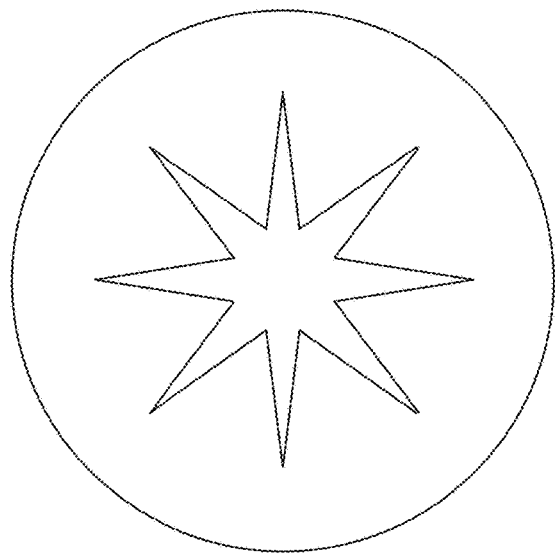
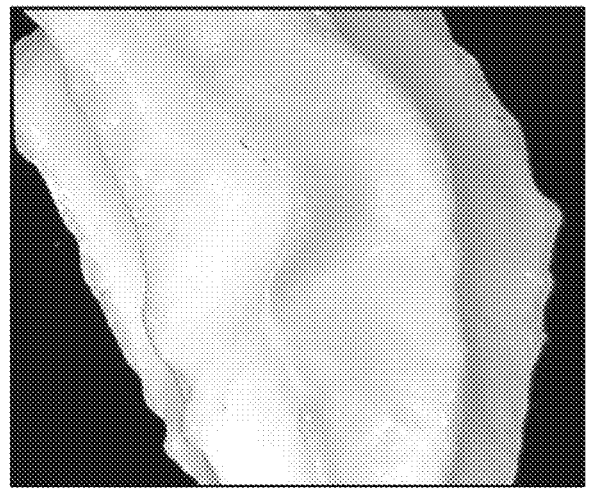
Fig. 15A  Fig. 15B
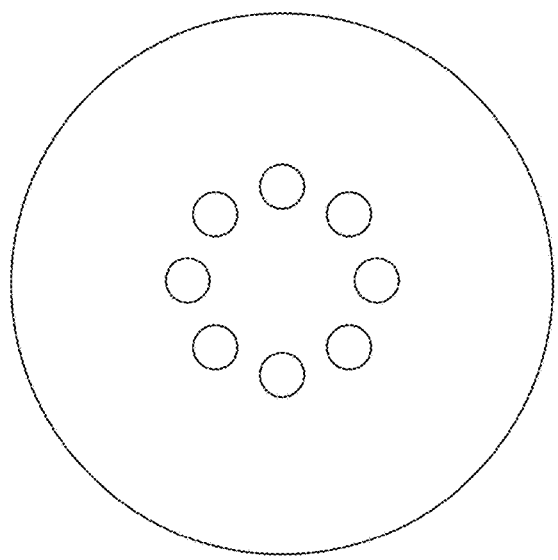
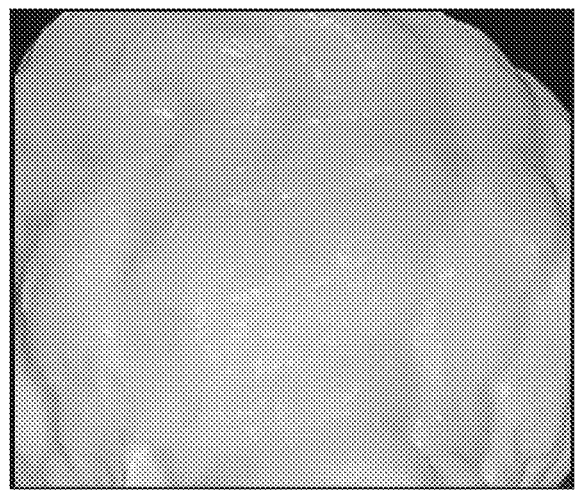
Fig. 16A  Fig. 16B

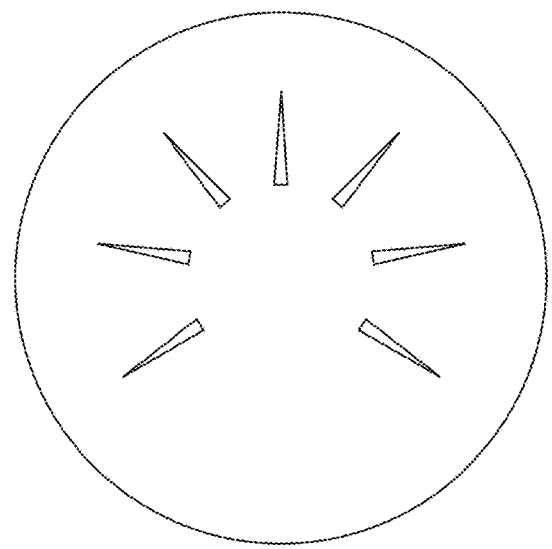 
Fig. 17A Fig. 17B
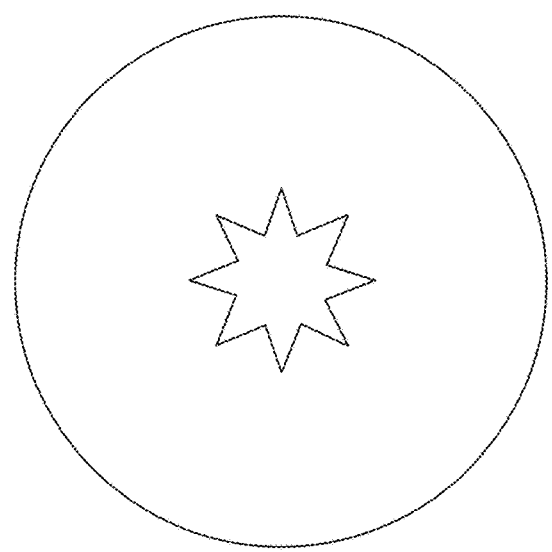 
Fig. 18A Fig. 18B

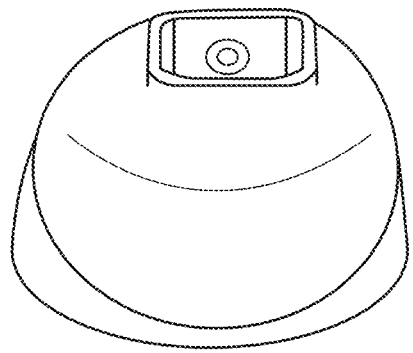
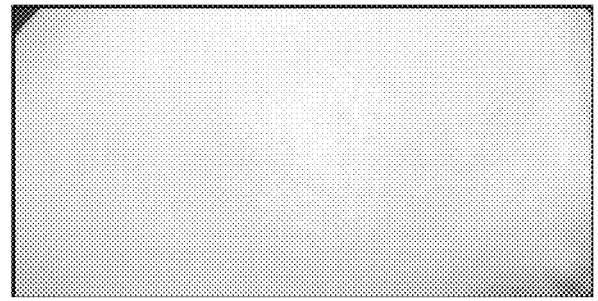
Fig. 19A
Fig. 19B
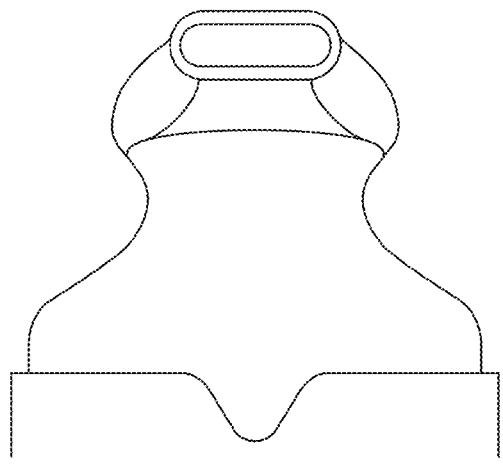
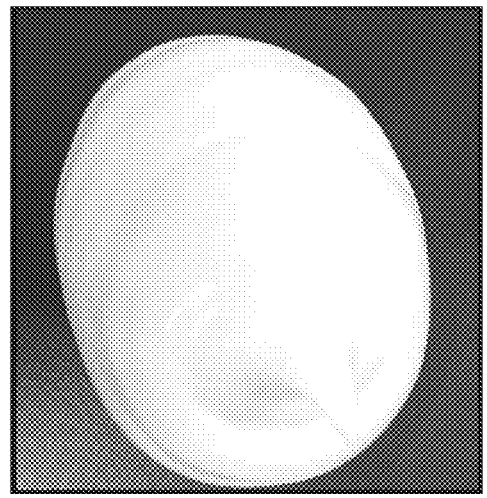
Fig. 20A
Fig. 20B

AEROSOL FOAM DISPENSER AND METHODS FOR DELIVERING A TEXTURED FOAM PRODUCT

FIELD OF THE INVENTION

The present invention relates to aerosol foam dispenser and a method for dispensing a foam composition with a shape and/or texture.

BACKGROUND OF THE INVENTION

Aerosol foam products are commonly used in personal care applications, such as styling mousses and hand washes. Although still a minority, there are aerosol products that correspond to in-shower applications such as shampoos, hair conditioners and body washes. Aerosol foams are generally dispensed as a white blob (i.e. a mass without a defined shape and/or texture).

Texturing the outer surface of the foam or shaping it in a desired shape can be appealing to consumers because it can (a) improve the in-use experience, (b) inform the user of a specific product benefit, and/or (c) signify a differentiated product. However, it is difficult to dispense a textured and/or shaped foam with shampoo, conditioner and body wash compositions.

First, when using these products, most consumers need to dispense a relatively large dose (e.g. about 4 g to about 10 g) over a relatively short time (e.g. 1 to 3 seconds). Therefore, the product can be dispensed at a relatively high flow rate (e.g. from about 2 to about 10 g/s), making the foam difficult to shape.

Second, it can be easier to shape stiff foams that have a relatively low density and/or small bubble size. However, stiff foams can be difficult to spread and consumers prefer a shampoo, hair conditioner, and/or body wash with a lower stiffness that is easier to spread.

It can be even more difficult to dispense a shaped and/or textured foam when the liquid composition is a compact composition with a relatively high concentration of surfactant and/or other actives. Compact shampoo, conditioner, and body wash compositions can have a low elastic modulus, which can make it difficult to dispense a textured/shaped foam and can cause the foam to collapse.

As such, there remains a need for an aerosol dispenser that can dispense a shampoo, hair conditioner, and/or body wash with a textured/shaped outer surface at an acceptable delivery rate.

SUMMARY OF THE INVENTION

A method of dispensing a textured foam from an aerosol container comprising: (a) providing an aerosol foam dispenser comprising: (i) a pressurizable outer container for storing a propellant and a composition under pressure; (ii) an actuator where the actuator is attached to a top of the outer container comprising: (1) a valve being movable to an open position to release a mixture of the aerosol and the composition; (2) a trigger for actuating the valve; (3) a nozzle comprising a nozzle surface comprising one or more shaping orifices; wherein said orifices are in fluid communication with the valve; (b) actuating the trigger; (c) dispensing a foam composition at a linear velocity; wherein the foam composition comprises an elastic modulus from about 10 Pa to about 200 Pa; wherein the method comprises a shape factor from about 0.11 to about 1. An aerosol foam dispenser comprising: (a) a pressurizable outer container for storing a propellant and a composition under pressure; (b) an actuator where the actuator is attached to a top of the outer container comprising: (i) a valve being movable to an open position to release a mixture of the aerosol and the composition; (ii) a trigger for actuating the valve; (iii) a nozzle comprising a nozzle surface comprising one or more shaping orifices; wherein said orifices are in fluid communication with the valve; wherein the nozzle surface comprises a space factor greater than 0.5.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 15A is the orifice used in Example E;
FIG. 15B is a photograph of the foam produced by the orifice in FIG. 15A in Example E;
FIG. 16A is the orifice used in Example F;
FIG. 16B is a photograph of the foam produced by the orifice in FIG. 16A in Example F;
FIG. 17A is the orifice used in Example G;
FIG. 17B is a photograph of the foam produced by the orifice in FIG. 17A in Example G;
FIG. 18A is the orifice used in Example H;
FIG. 18B is a photograph of the foam produced by the orifice in FIG. 18A in Example H;
FIG. 19A is the orifice used in Example I;
FIG. 19B is a photograph of the foam produced by the orifice in FIG. 11A in Example I;

FIG. 20A is the orifice used in Example J; and

FIG. 20B is a photograph of the foam produced by the orifice in FIG. 11A in Example J.

DETAILED DESCRIPTION OF THE INVENTION

Figure 1:
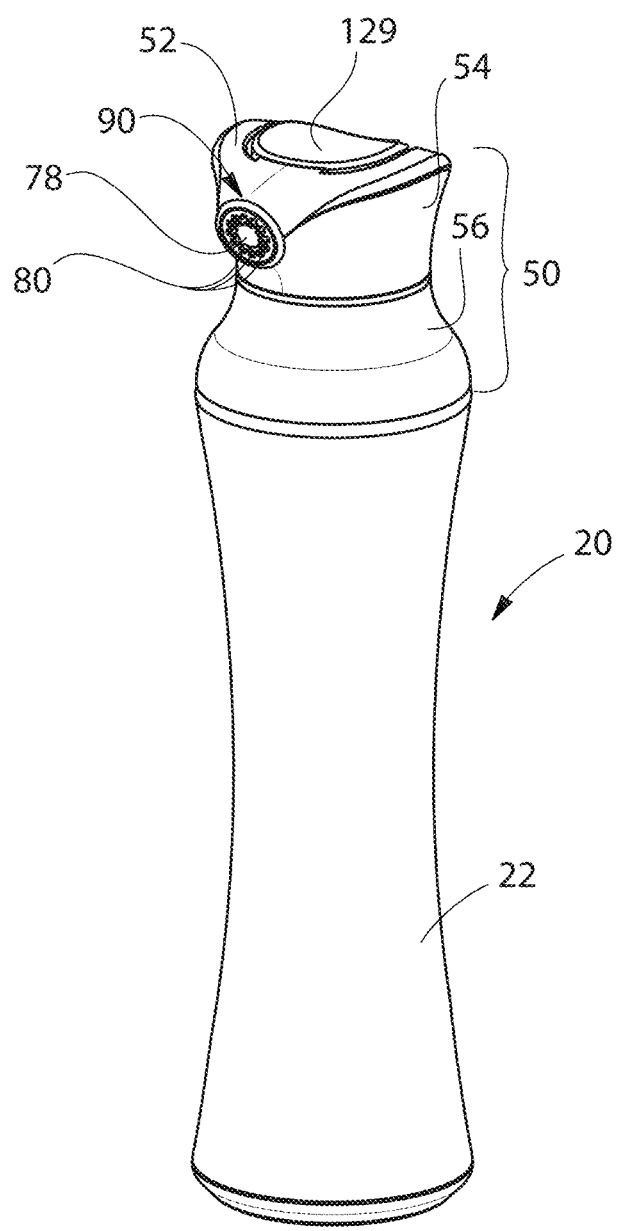
FIG. 1 is a perspective view of an aerosol dispenser.

While the specification concludes with claims particularly pointing out and distinctly claiming the invention, it is believed that the present disclosure will be better understood from the following description.

Many consumers want shampoo, conditioner, and/or body wash dispensed as an aerosol foam. Some consumers think these products are easier to use and spread more easily across the body, hair, and/or scalp, which can ultimately enhance the user's experience and lead to better cleaning and/or conditioning results. Current foam products are generally dispensed as a white blob (i.e. a shapeless mass), which consumers can find unappealing. Texturing the outer surface of the foam or shaping it in a desired shape can be beneficial (a) to improve the in-use experience, (b) to inform the user of a specific product benefit, or (c) to signify a differentiated and/or premium product including signifying the brand/logo through the orifice shape.

However, delivering a textured and/or shaped foam for a foam shampoo, hair conditioner and/or body wash is challenging for at least the following reasons:
(1) Shampoos, conditioners, and/or body washes generally require a relatively high amount of product for a typical job (e.g. between 4 to 10 g), which leads to high flow rates (e.g. in the range of 2-10 g/s) to maintain an acceptably short dispensing time (e.g. between 1 and 3 seconds). This high flow rate can lead to accumulation of the foam products around the orifice, which can make the foam difficult to shape.
(2) To be easily spreadable, the foam shampoo, conditioner, and/or body wash can have a lower stiffness (i.e. relatively low elastic modulus (G')). However, it is generally easier to shape stiff foams (having low density and/or small bubble size).

It has been found that the aerosol dispenser in combination with the compositions described herein, can deliver a consumer acceptable textured and/or shaped foam product.

A foam can contain a high-volume fraction of gas dispersed in a liquid. When a foam is subjected to compressive stresses typical of an extrusion process, the foam structure can undergoes different regimes. At low stresses/strain, the deformation can show a regime of linear elasticity followed by a long collapse plateau. This regime is truncated by a regime of densification in which the stress rises steeply. At large compressive strains the opposite walls of the cells can crush together and the cell wall material itself is compressed: then the stress-strain curve rises steeply tending to a slope of the Young modulus of the propellant at a limiting strain.

To form a foam with a distinguishable shape/texture from the shampoo, conditioner, and/or body wash compositions described herein, it was found that the nominal strain of the flow areas adjacent to the outlet can be limited about 60-80% of the limit strain to maintain the foam texture and avoid foam collapse. When this limit is exceeded the foam cells adjacent to the orifice outlet can crush and the foam can lose its shape/texture.

The Shape Factor can describe the ability of the one or more shaping orifices to imprint an outer portion of a foam stream into a shape/texture and the ability of the one or more shaping orifice(s) to produce one or more foam streams that do not collapse or crush. An empirical equation describing the relationship is found hereafter. The shape factor can vary from about 0.11 to about 1, alternatively from about 0.12 to about 0.75, alternatively from about 0.13 to about 0.5, alternatively from about 0.15 to about 0.45, alternatively from about 0.16 to about 0.40, alternatively from about 0.17 to about 0.37, and alternatively from about 0.20 to about 0.37.

The nozzle surface can have one or a plurality of orifices. The 'external convex hull' or 'convex envelop' is the smallest convex set that contains all orifices. The shaping orifice(s) are the orifices in contact with the external convex hull. In some examples, there can be 'central orifices,' which are orifices that are not in contact with the external convex hull. The central orifice(s) may not contribute to imprinting a texture/shape to the foam extrudate. In some examples, there can be one central orifice located at approximately the center of the nozzle surface and/or convex envelop. The 'corolla' is the area comprised between the external convex hull and the inner convex hull (the inner convex hull is the maximum convex set contained inside the external convex hull and the shaping orifices). The area comprised inside the inner convex hull is defined 'central' area. Based on these definitions, the 'convex envelop area' equals the sum of the 'corolla' and 'central' areas. The 'total orifice area' equals the sum of the 'shaping orifice(s)' and the 'central orifice(s).'

The shaping orifices can be the same size and shape and can be spaced evenly apart. Alternatively, the shaping orifices can have various sizes, shapes, and uneven spacing. One or more shaping orifices can have at least a side with a convex shape and/or concave. In some examples, one or more orifices is convex and does not have a portion that is concave, for instance the one or more orifices can be circular, oval, triangular, and other convex polygons. The shaping orifices can be at least about 1 mm apart.

A plurality of shaping orifices can be the nozzle surface in a ring configuration or an arch. Optionally, there can be orifices inside the ring or arch configuration. In one example, a non-shaping orifice can be located at the center of the nozzle surface.

The area of the one or more shaping orifices can have an area from about 27 $mm^2$ to about 120 $mm^2$, alternatively from about 29 $mm^2$ to about 110 $mm^2$, alternatively from about 30 $mm^2$ to about 100 $mm^2$, alternatively from about 31 $mm^2$ to about 95 $mm^2$, and alternatively from about 35 $mm^2$ to about 60 $mm^2$. The shaping orifice area can be determined from critical dimensions of the cross-section and Euclidian geometry including using computer-aided drafting tools such as SolidWorks™.

The foam as it exits the shaping orifices can have a linear velocity. Generally, if the linear velocity is too fast, it can become hard to shape the foam. However, due to the relatively large amount of shampoo, conditioner, and body wash that one needs to clean and/or condition his or her hair and/or skin, the linear velocity cannot be too slow. Thus, the linear velocity needs to be relatively fast to be consumer acceptable, while still permitting the foam to be shaped/textured. The dispenser can have a linear velocity from about 0.5 m/s to about 2.4 m/s, from about 0.5 m/s to about 1.94 m/s, alternatively from about 0.55 m/s to about 1.935 m/s, alternatively from about 0.6 m/s to about 1.925 m/s, alternatively 0.631 mm/s to about 1.910 m/s, and alternatively from about 1.0 m/s to about 1.714 m/s.

The area of the corolla is linked to the Space Factor and can be calculated using SolidWorks™ or similar program. The corolla of the shaping orifices can have an area from about 51 $mm^2$ to about 225 $mm^2$, alternatively from about 55 mm² to about 215 mm², alternatively from about 60 mm² to about 200 mm², alternatively from about 70 mm² to about 190 mm², alternatively from about 80 mm² to about 185 mm², alternatively from about 85 mm² to about 177 mm², alternatively from about 100 mm² to about 177 mm², alternatively from about 125 mm² to about 177 mm². The corolla can have an area greater than 50 mm², greater than 60 mm², greater than 80 mm², and/or greater than 100 mm².

Nozzle shape factor is a non-dimensional index of a value between 0 and 1. It describes the effectiveness of a nozzle geometry to contain the nominal strain during the foam extrusion for a given foam type and achieve a measurable consistent foam texture or shape. The nozzle shape factor can be described using the following empirical formula:

$$\text{Shape Factor} = (\text{Space} \cdot (1-\alpha) + \text{AR} \cdot \alpha) \cdot f(v)$$

Where:
Space is the nozzle space factor;
AR is the nozzle aspect ratio;
$\alpha$ is the foam stiffness factor; and
wherein $f(v)$ is a function of the foam speed factor during dispensing.

As used herein "nozzle space factor" (Space) describes the areal ratio of the one or more shaping orifice and the corolla. The space factor is an indication if you have multiple shaping orifices how spread apart the geometry is across the nozzle surface. If the streams are separated, the foam is less likely to collapse. However, if the streams are too far apart, the dispenser may dispense foam that is highly separated, potentially resembling spaghetti, which is not consumer preferred. The space factor can be determined using the following formula:

$$\text{Space} = \frac{\text{area (Corolla)} - \text{area (Shaping orifices)}}{\text{area (Corolla)}}$$

For the nozzle surface and shaping orifices described herein, the space factor can be from about 0.2 to about 0.8, alternatively from about 0.22 to about 0.75, alternatively from about 0.24 to about 0.72. The space factor can be from about 0.5 to about 0.85, alternatively from about 0.6 to about 0.7, alternatively from about 0.65 to about 0.75. The space factor can be greater than 0.2, greater than 0.25, greater than 0.4, greater than 0.5, and/or greater than 0.6.

As used herein the "nozzle aspect ratio" (AR) is linked to the effectiveness of the one or more shaping orifices to extrudate the foam flow into a targeted shape and/or texture. The higher the nozzle aspect ratio, the higher the shear stress of the foam extrudate. For a single shaping orifice, the nozzle aspect ratio is calculated by multiplying the frequency to the amplitude of the orifice boundary. When one or more shaping orifices are present, this factor is calculated by weighting the different contributions by the area of each shaping orifice as it is shown below.

$$AR = \frac{\sum_{i=1}^{n} Freq_i \times Amp_i \times Area_i}{\sum_{i=1}^{n} Area_i}$$

Where:
$Freq_i$ is the frequency of the vibration;
$Amp_i$ is the amplitude of the vibration; and
$Area_i$ is the area of the surface orifices;

For the nozzle surface with shaping orifices described herein, the nozzle aspect ratio can be from about 0 to about 0.45. In another example, the nozzle aspect ratio can be greater than 0 and less than 0.5.

The frequency of the vibration ($Freq_i$) can be determined as follows. Notches describe the non-convex parts of a polygon. The maximum number of notches that occur on a polygon (pol) depend on its number of vertices. If notches and vertices describe the number of vertices ad the number of notches, respectively, the following property will hold:

$$\text{notches(pol)} \leq \text{vertices(pol)} - 3$$

Therefore, the number of notches can be normalized to the interval [0,1] by $$\text{notches}_{norm}(pol) = \frac{\text{notches}(pol)}{\text{vertices}(pol) - 3}$$

The edges of polygons with a high frequency of the vibration change their direction very often. The fewer notches that occur, the smoother the boundary. If $\text{notches}_{norm}$ is 0, the polygon is convex. Similar to low values of $\text{notches}_{norm}$ high values indicate a smooth boundary. In the extreme case, where every edge has a direction different from that of its predecessor, $\text{notches}_{norm}$ is about 0.5.

For the nozzle surface with shaping orifices described herein, $\text{Notches}_{norm}$ can be from about 0 to about 0.75, alternatively 0 to about 0.7, alternatively 0 to about 0.67.

To determine the frequency of the vibration $\text{notches}_{norm}$ is transformed by the following equation:

$$\text{freq}(pol) = 16(\text{notches}_{normal}(pol) - 0.5)^4 - 8(\text{notches}_{norm}(pol) - 0.5)^2 + 1$$

For the nozzle surface with shaping orifices described herein, the frequency of the vibration can be from about 0 to about 1, alternatively from about 0 to about 0.9.

The Amplitude of the Vibration ($Amp_i$) can be determined as follows. The frequency of the vibration makes no statement with respect to the intensity of the vibration. To quantify this amplitude, the increase of the boundary of the polygon is compared to the boundary of its convex hull. The following equation describes the amplitude vibration:

$$ampl(ori) = \frac{\text{boundary}(ori) - \text{boundary}(convexhull(ori))}{\text{boundary}(ori)}$$

If the orifice is convex, then ampl=0 and if the boundary is very long then ampl~1.

For the nozzle surface with shaping orifices described herein, amplitude of the vibration can be from about 0 to about 0.5.

Additional information regarding measuring complex polygonal objects can be found T. Brinkhoff, H.-P. Kriegel, R. Schneider, A. Braun, "Measuring the complexity of polygonal objects", *Proceedings of the Third ACM International Workshop on Advances in Geographical Information Systems*, pp. 109-117, 1995, incorporated by reference.

As used herein "foam stiffness factor" ($\alpha$) is a non-dimensional factor comprised between 0 and 1 function of the foam elastic modulus (G') calculated as follows:

$$\alpha(G') = \frac{1}{1 + e^{-k(G' - G'_0)}}$$

Where:
G' is the foam stiffness or storage modulus (Pa);
G'$_0$ is a constant=176 Pa and
k is a constant=0.0095 1/Pa The lower α, the more difficult is to imprint the foam extrudate by exerting high shear at the orifice. The higher α, the easier it is to achieve a shape by extruding the foam. α is approximately 0.2 for compliant foams (with G'~30 Pa) and for stiff foams (with G'~400 Pa), c is approximately 0.9.

As used herein "foam speed factor" (f(v)) is a non-dimensional modifier of the foam shape factor, dependent on the linear velocity (L, mm/s). The relationships between the nominal strain and stress and the speed of the foam at the outlet are quite complex in nature. However, empirically we have found that:

f=600/L, if v is below 600 mm/sec.
f=1, if L is equal or larger than 600 mm/sec

As used herein, "linear velocity" (mm/s) is calculated as follows:

$$L = \frac{D}{\rho(0) \cdot S_{TOT}} \cdot 1000, \left(\frac{mm}{s}\right)$$

Where:
D=delivery rate, g/s
ρ(0)=instantaneous foam density, g/cc
$S_{TOT}$=Total orifice area, mm$^2$ The delivery rate can be determined by ASTM D3069 (2005).

The instantaneous foam density can be calculated using the Instantaneous Foam Density Method, described hereafter.

The shaping orifice area is the total area of the shaping orifices and can be determined from critical dimensions of the cross-section and Euclidian geometry including using computer-aided drafting tools such as SolidWorks™. The shaping orifice area can be from about 25 mm$^2$ to about 120 mm$^2$, alternatively from about 30 mm$^2$ to about 110 mm$^2$, alternatively from about 40 mm$^2$ to about 100 mm$^2$, alternatively from about 50 mm$^2$ to about 97 mm$^2$, and alternatively from about 55 mm$^2$ to about 95 mm$^2$.

Aerosol Dispenser

Figures 2, 3, 4:
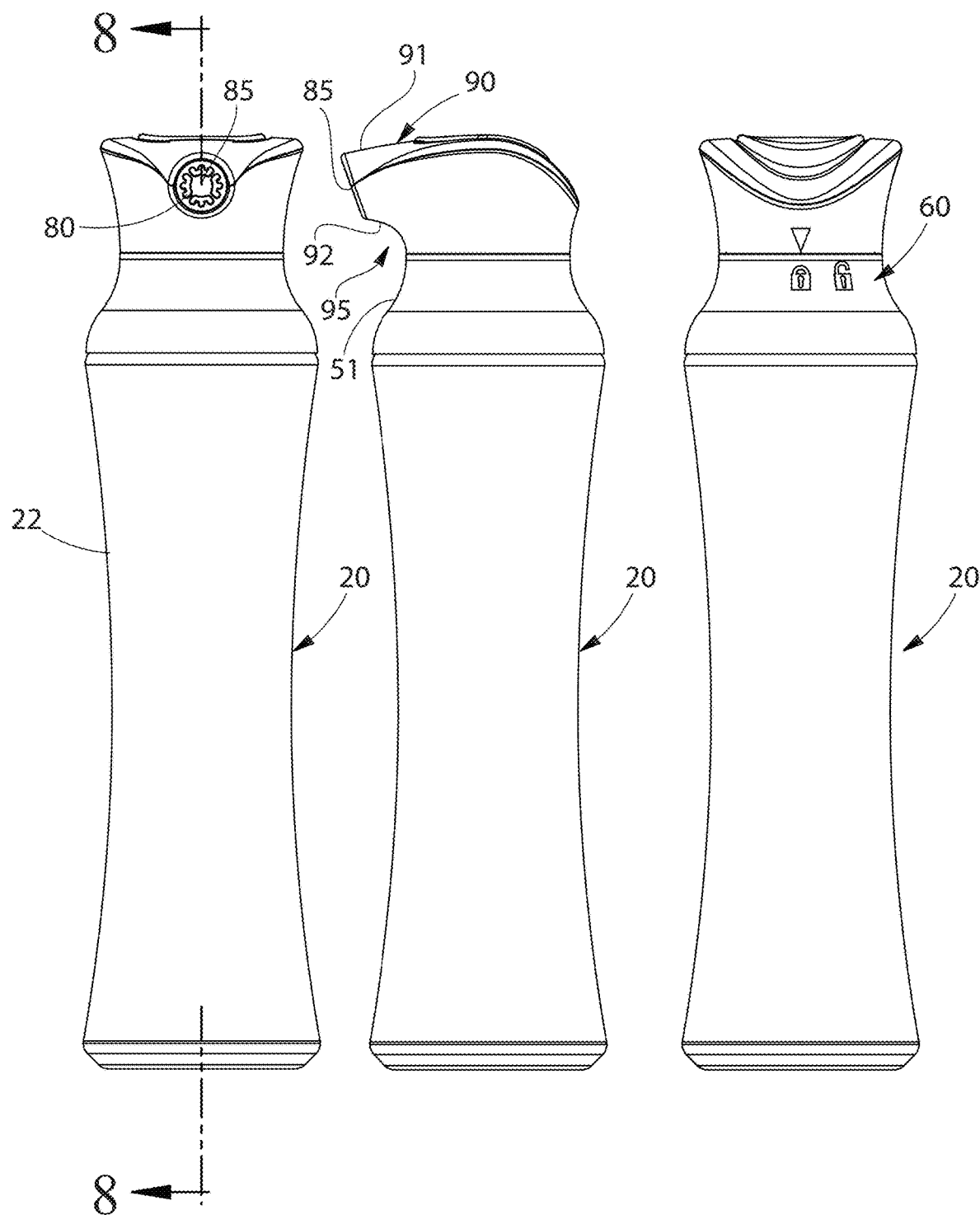
FIG. 2 is a front view of the dispenser of FIG. 1.
FIG. 3 is a left side of the dispenser of FIG. 1.
FIG. 4 is a rear view of the dispenser of FIG. 1.

Referring to FIGS. 1 and 2, an aerosol dispenser 20 is shown. The aerosol dispenser 20 can comprise a pressurizable outer container 22 and actuator 50 usable for such a dispenser 20. The actuator 50 can include a shroud 56, an actuator body 54, and a toupee 52. The shroud 56, actuator body 54, and toupee 52 can be a single piece and/or separate pieces. The toupee 52 can also include a trigger 129 that may be used to dispense product through the one or more shaping orifices 80 at the point of use. The shaping orifices 80 can be at the distal end of the nozzle 90 and can be on the nozzle surface 78. The nozzle surface can be flat or primarily flat. In other examples, the nozzle surface can be concave and/or convex. The nozzle 90 can be an integrated with toupee 52 and/or actuator body 54 or it can be a separate component.

The trigger 129 can be pressed down with a user's finger, generally the index finger on the user's dominant hand and in other instances, the user's thumb on the user's dominant hand. The user's finger can be planar with the trigger's surface and will actuate the trigger at an actuation direction. In the example in FIGS. 1-10, trigger 129 is a button at the top of the actuator. In other examples, the trigger could be a trigger spray and/or located in a different position on the actuator.

The outer container 22 may be injection stretch blow molded (ISBM). Additionally, the containers 22 may be injection blow molded or extrusion blow molded. If ISBM is selected, a 1 step, 1.5 step or 2 step process may be used.

Figure 5:
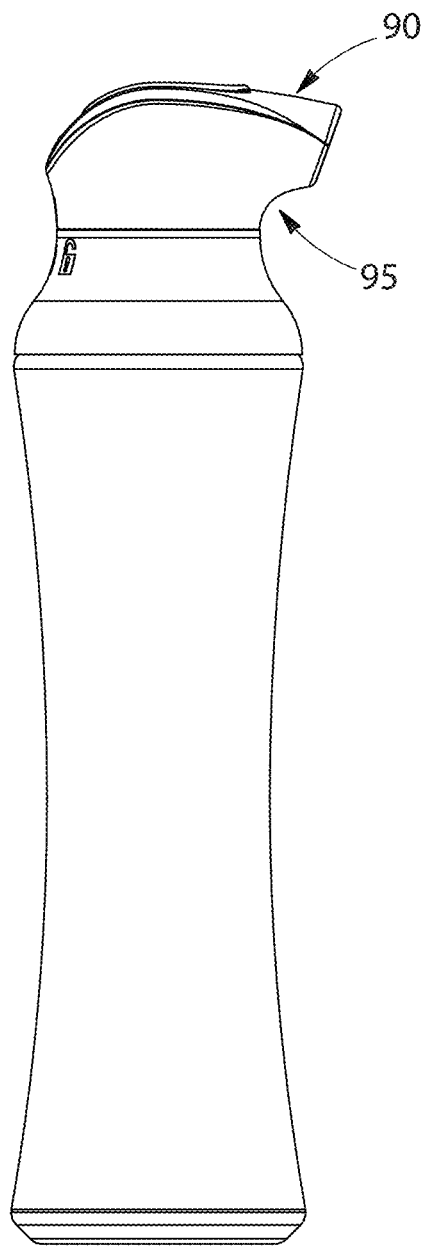
FIG. 5 is a right side view of the dispenser of FIG. 1.
Figure 6:
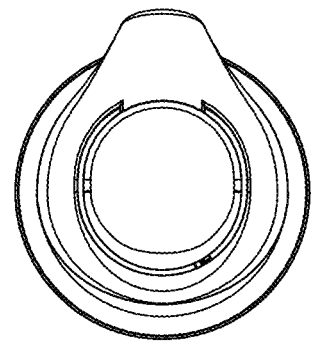
FIG. 6 is a top view of the dispenser of FIG. 1.
Figure 7:
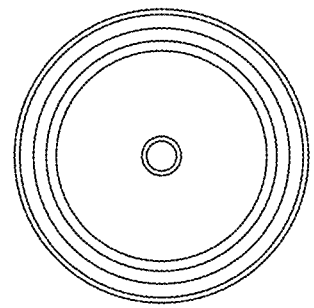
FIG. 7 is a bottom view of the dispenser of FIG. 1.
Figure 11A:
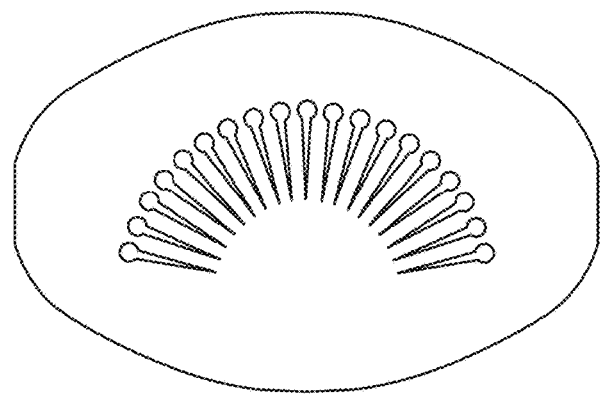
FIG. 11A is the orifice used in Example A.
Figure 11B:
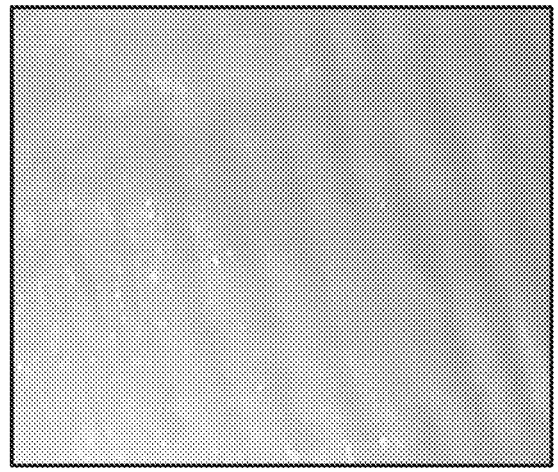
FIG. 11B is a photograph of the foam produced by the orifice in FIG. 11A in Example A.

FIGS. 3 and 5 show a left side view and a right side view, respectively, of aerosol dispenser 20. The side views show nozzle 90 extending longitudinally from aerosol dispenser 20. Nozzle 90 has a top surface 91 and a bottom surface 92. In this example, the bottom surface 92 and outer surface of the actuator 51 can create overhang 95. In another example, the bottom surface of the nozzle and the outer container can create the overhang. Overhang 95 can be adapted so the consumer can at least a portion of a finger, in particular the side of the little finger, of the receiving hand underneath the nozzle, as shown in FIG. 11. In one example, the overhang is adapted to receive about half of an adult's little finger.

FIG. 4 shows a rear view of aerosol dispenser 20 with locking mechanism 60.

Figure 8:
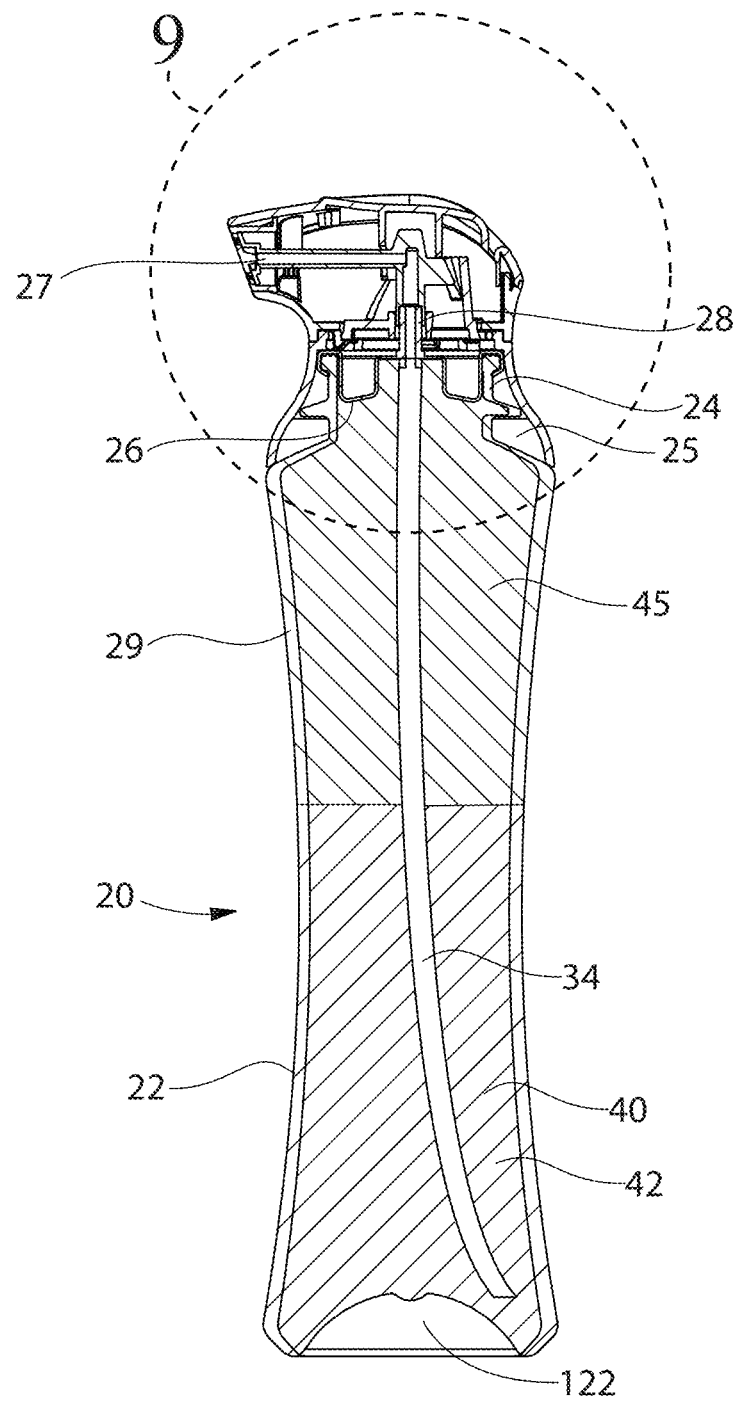
FIG. 8 is a cross-sectional view of the aerosol dispenser of FIG. 2 along line 8.
Figure 9:
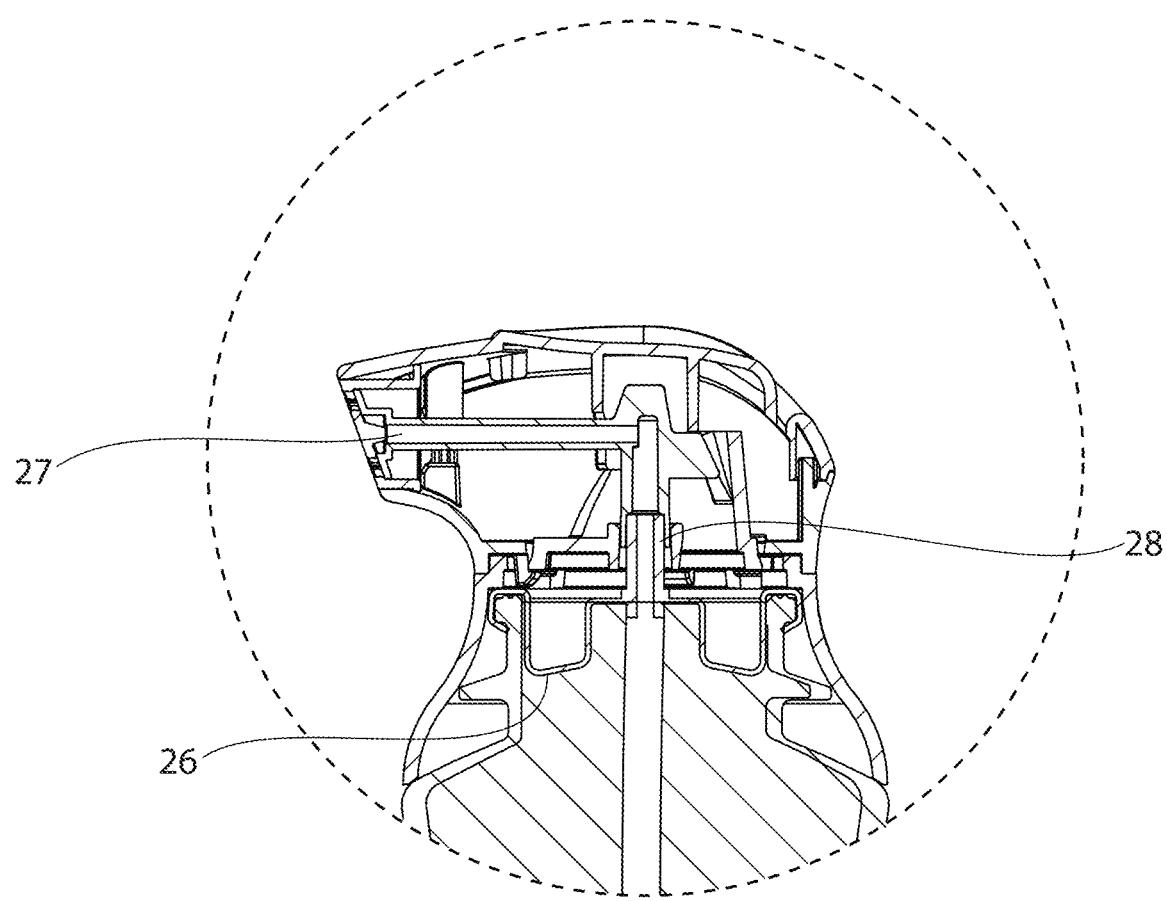
FIG. 9 is an enlarged cross-sectional view of section 9 in the aerosol dispenser of FIG. 8.

FIGS. 8 and 9 shows a cross-sectional view of the dispenser of FIG. 2 along line 8. This aerosol dispenser may comprise a dip tube 34. The dip tube 34 extends from a proximal end sealed to the valve stem 28. In other examples, a female valve can be used. The dip tube 34 may terminate at a distal end juxtaposed with the bottom of the outer container 22. This embodiment provides for intermixing of the product 42 and propellant 40. Between the surface of the product and the valve stem 28 is headspace 45 that contains a vaporized portion of propellant 40.

In another example, a collapsible, flexible bag may be sealed to the opening on the underside of the valve cup or may be placed between the valve cup and the container. This bag limits or even prevents intermixing of the contents of the bag and the components outside of the bag. Thus, product may be contained in the bag. Propellant may be disposed between the outside of the bag and the inside of the outer container. Upon actuation of the valve, a flow path out of the bag is created. Gage pressure from the propellant disposed between the bag and the outer container causes pressurization of the product, forcing the product to flow into ambient pressure. This embodiment is commonly called a bag on valve or bag in can and may be used.

The foamer can be an upright aerosol pump style actuator i.e. where the nozzle is located about at the same level or above the liquid meniscus during dispensing, as in FIGS. 1-10. In another example, the foamer can be an inverted aerosol pump style actuator i.e. where the nozzle is located below the liquid meniscus during dispensing. In this case, the container can include a can or bottle fixed to a (discharge) valve for inverted use. In either case, the container can include a barrier aerosol that can include bag-on-valve, bag-in-can, bag-in-bottle and piston aerosols. In another example, a mousse valve may be crimped to the container.

As seen in FIG. 8, the outer container 22 may sit on a base 122. The base is disposed on the bottom of the outer container 22 and of the aerosol dispenser 20. Suitable bases include petaloid bases, champagne bases, hemispherical or other convex bases used in conjunction with a base cup, as shown in US publication 2009/0050638A1. In the example in FIG. 8, there is a champagne base, which can remain pushed up into the bottle, as shown, even when the container is used under pressure.

Referring to FIGS. 8 and 9, the aerosol dispenser 20 may comprise a valve cup 26 for holding a valve stem 28 and/or dip tube 34. A plastic or metal valve cup 26 may be sealed to the opening of the outer container 22. A valve stem 28, in turn, may be disposed within the valve cup 26. The valve stem 28 provides for retention of product 42 within the aerosol dispenser 20 until the product 42 is selectively dispensed by a user. The valve stem 28 may be selectively actuated by a trigger. When the trigger is actuated it can move the valve stem to an open position allowing a mixture of product 42 and propellant 40 to move past the valve stem 28, into a dispensing channel 27, and through an orifice. The orifice can be the dispensing orifice or it can be fluidly connected to the dispensing orifice, ultimately dispensing the composition as a foam. The dispensing channel 27 and/or nozzle and/or nozzle surface can be in a fixed position relative to the outer container 22 during dispensing.

Referring to FIGS. 1-10, the aerosol dispenser 20, and components thereof, particularly the outer container 22, may have a round cross section, for improved pressure control. The sidewall 29 of the outer container 22 may be arcuate, and particularly have an oval or round cross section. Alternatively, the outer container 22, and particularly the neck 24, shoulder 25 and/or body thereof, etc., may be eccentric and have a square, elliptical, oval, irregular or other cross section. Furthermore, the cross section may be generally constant or may be variable, as shown. If a variable cross-section is selected, the outer container 22 may be teardrop shaped, spherically shaped, barrel shaped, hourglass shaped, contoured, or monotonically tapered.

The outer container 22 may range from about 100 mm to about 210 mm in height, taken in the axial direction and from about 50 to about 65 mm in diameter if a round footprint is selected, with other geometries also being feasible. The outer container 22 may have a volume ranging from 150 to 525 mL exclusive of any components therein. The outer container 22 may be injection stretch blow molded. If so, the injection stretch blow molding process may provide a planar stretch ratio greater than about 8, 8.5, 9, 9.5, 10, 12, 15 or 20 and less than about 40, 30 or 25.

The outer container 22 may be pressurized to an internal gage pressure of 100-1150, kPa and discharged to a final propellant 40 gage pressure of 0 to 120 kPa. The pressurizeable container 22 may include a propellant 40. Any suitable propellant 40, including those propellants, which can also be referred to as a blooming agent, described hereafter, may be used.

Referring to FIGS. 1-10, the outer container 22 may comprise a plastic pressurizeable container. The plastic may be polymeric, and particularly substantially or entirely comprise polyethylene terephthalate (PET) and/or polyethylene naphthalate (PEN). The outer container 22 can be colorless and/or colored. The valve assembly 28, and valve cup 26 may be welded to the neck 24 of the outer container 22.

Referring to FIGS. 1-10, if desired, the outer container 22, valve cup 26, and/or other components of the aerosol dispenser 20 may be made of sustainable materials and/or combinations and blends of sustainable and other materials. Suitable sustainable materials include polylactic acid (PLA), polyglycolic acid (PGA), polybutylene succinate (PBS), an aliphatic-aromatic copolyester optionally with high terephthalic acid content, an aromatic copolyester optionally with high terephthalic acid content, polyhydroxyalkanoate (PHA), thermoplastic starch (TPS) and mixtures thereof. Suitable materials are disclosed in commonly assigned U.S. Pat. No. 8,083,064.

If desired, the outer container 22 and/or dip tube 34, may be transparent or substantially transparent. If the outer container 22 is transparent, this arrangement provides the benefit that the consumer knows when product 42 is nearing depletion and allows for improved communication of product 42 attributes, such as color, viscosity, position of the liquid meniscus vs. the dip tube inlet, etc. If the outer container is transparent or substantially transparent, the dip tube may be also colored to achieve a visual break from the product. This can help to make the dip tube inlet even more visible by consumers. Also, labeling or other decoration of the container may be more apparent if the background to which such decoration is applied is clear. Alternatively, or additionally, the outer container 22 may be transparent and colored with like or different colors.

FIG. 10 is an exploded perspective view of aerosol dispenser 22. Actuator 50 includes toupee 52, nozzle component 75, manifold 65, actuator body 54, and shroud 56 and in this example, these components are all separate. In other examples, some or all of these components could be a unitary piece.

Nozzle component 75 includes nozzle surface 78 and shaping orifices 80. Nozzle component 75 in combination with a portion of the toupee 52 forms nozzle 90. Nozzle component can fit under toupee 52. Nozzle component 75 could allow different nozzle components with different shaping orifices to be interchanged during manufacturing, allowing different shaped foams for different products.

Figure 10A:
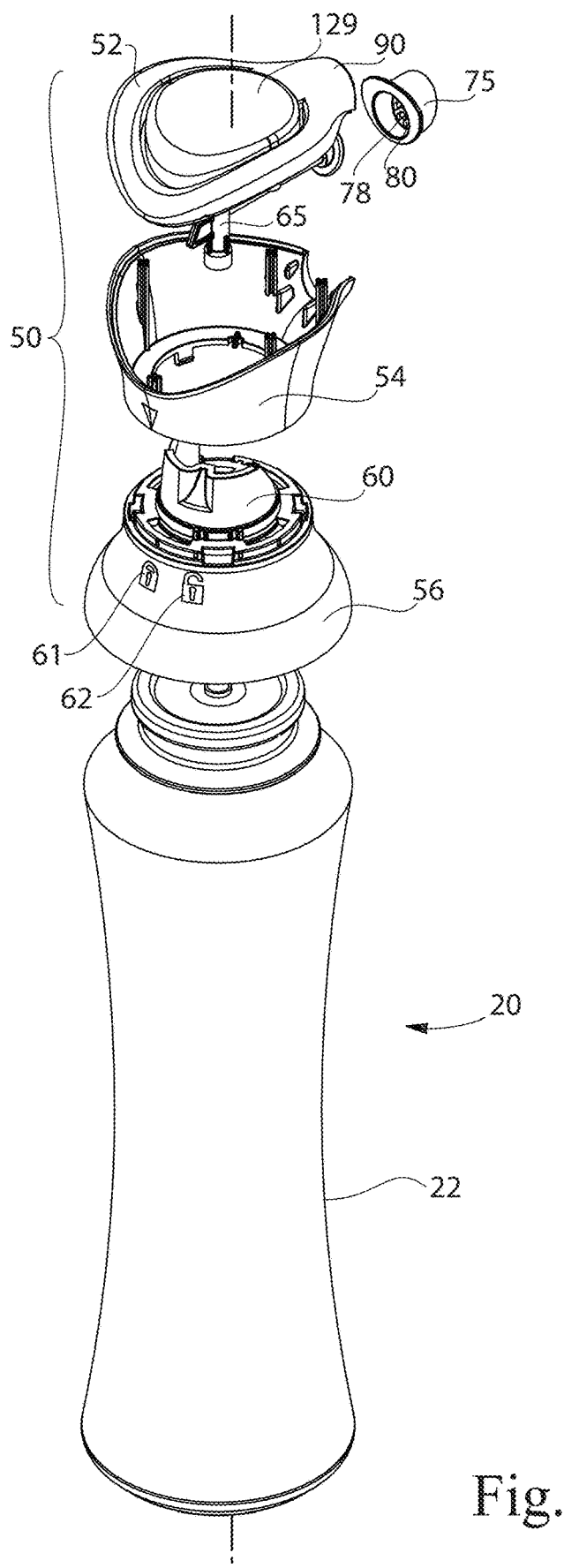
FIG. 10 is an exploded perspective view of the aerosol dispenser of FIG. 1.
FIG. 10B is the underside of the toupee in FIG. 10A.
FIG. 10C is a sectioned view of the dispenser in the locked position.
FIG. 10D is a sectioned view of the dispenser in the unlocked position.
FIG. 10E is a sectional view of the latching mechanism between the shroud and the actuator body.
Figure 10B:
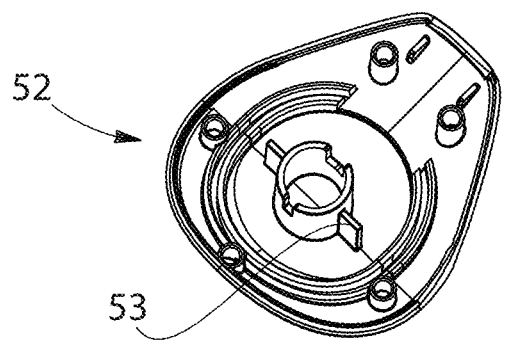
Figure 10C:
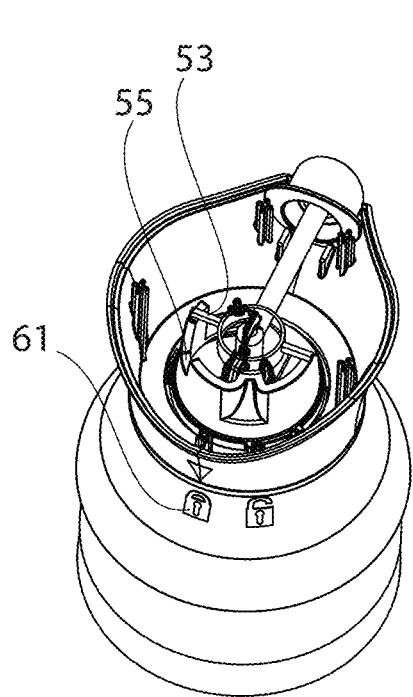
Figure 10D:
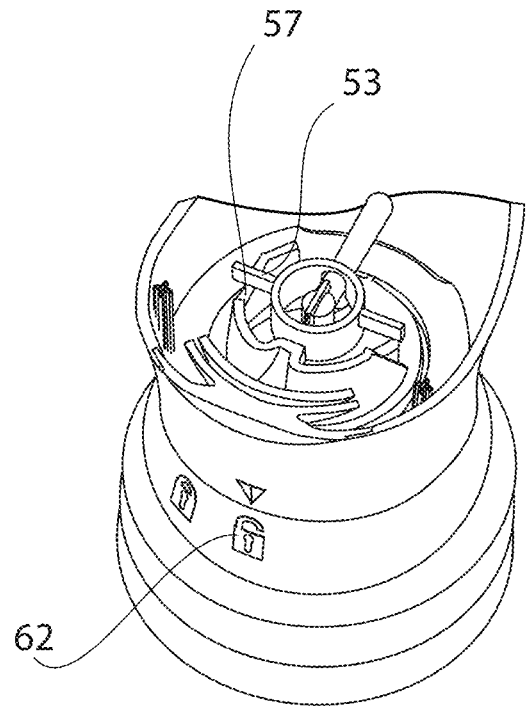

The actuator can include different systems to prevent accidental actuation before the first use (e.g. in distribution) or between uses (e.g. while carrying the aerosol in a gym bag). Twist lock mechanisms can be compatible with the actuator designs described in this invention due to the difficulty to cover nozzles with a pronounced overhang with an over-cap. FIGS. 10B-10E show the components of the twist lock mechanism formed by shroud 56 in combination with toupee 52 and actuator body 54 forms locking mechanism 60. FIG. 10B is the underside of toupee 52 and includes ribs 53. In other examples, the ribs can be on the manifold. As shown in FIG. 10C, when shroud 56 is in the locked position 61 the ribs 53 rest on shelf 55 preventing actuation by preventing the trigger from depressing. As shown in FIG. 10D, when shroud 56 is rotated (in this example by approximately 20° and in another example about 50°) to unlocked position 62 relative to the shroud, the ribs 53 are free to drop into groove 57, allowing actuation.

The shroud can be rigidly secured to the outer container. In one example, the shroud can be secured by engaging a plurality of lock beads that irreversible snap fit to the outer container. The shroud can be rigidly secured by 3-4 contact points.

Figure 10E:
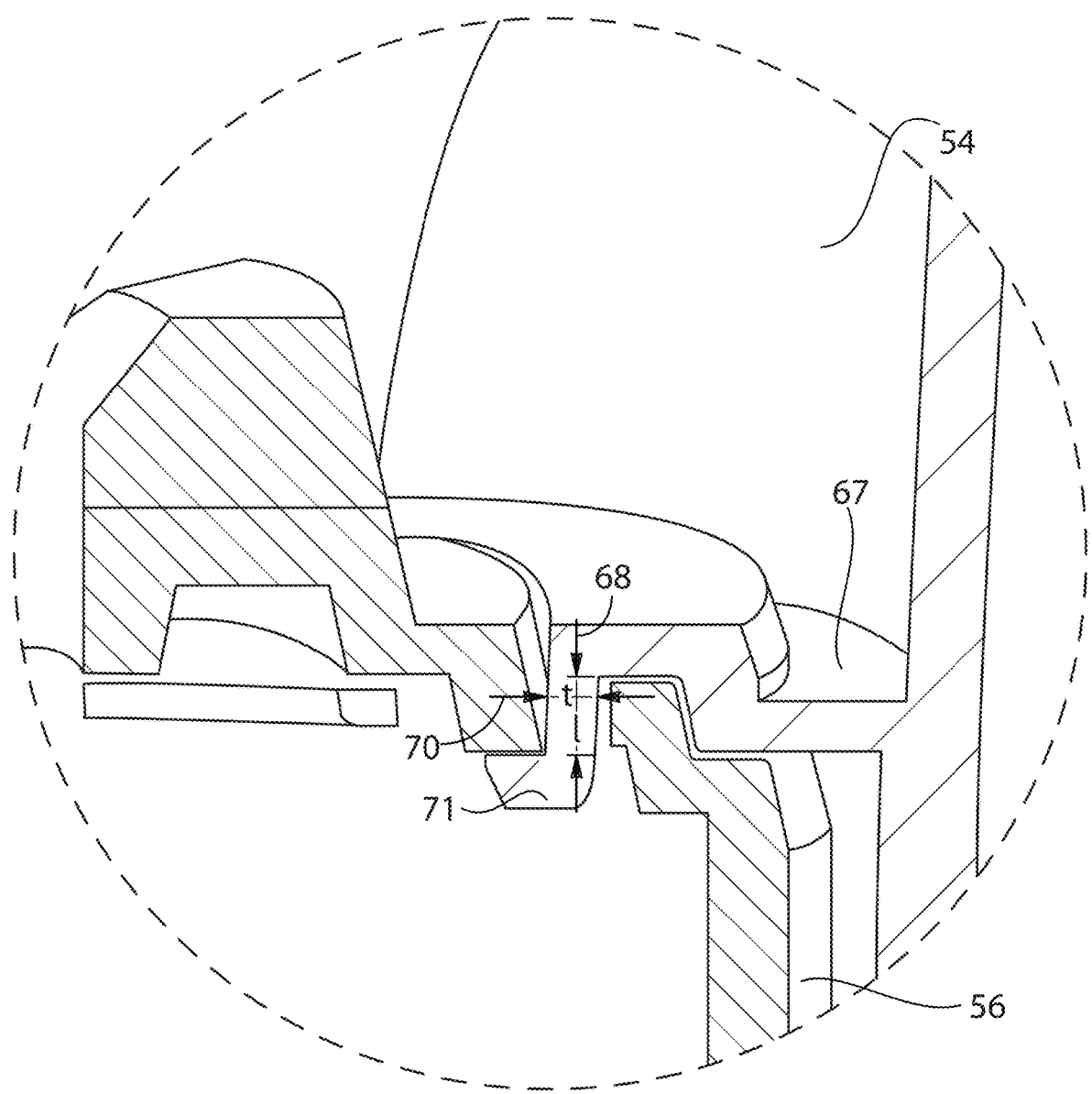

Furthermore, as shown in FIG. 10E, the shroud 56 and the actuator body 54 can be engaged by means of a latching mechanism inhibiting the separation of the shroud 56 from the actuator body 54 but allowing the rotation of the actuator body relatively to the shroud between the lock and the unlock position with virtually no tilting. This latching mechanism includes one or more non-releasing lock beams 68 extending from an actuator body inner platform 67 and characterized such that the beam length (l) from the base to the hook is about 1 to about 2 times the beam thickness (t) at the base 70. The beams 68 engage an equal number of slots built into the shroud. The number of beams and slots can vary based on the desired angle between the locked and unlocked position. In the specific example, four beams engage four slots to achieve about a 20° angle. In another example, three beads engage three slots to achieve about 50° angle between the unlocked to the locked position.

The latching mechanism can include beams that maintain the contact with the slots irrespective of whether or not that the dispenser is actuated. This construction can provide at least the following advantages: (1) the actuator body has substantially no tilt during actuation, as the actuation action is carried by the engagement of the trigger directly on the manifold. This was found to significantly improve control dispensing control, (2) a significantly improved separation force between the actuator body and the shroud preventing accidental disengagement/unlocking in the supply chain or during use and (3) a higher opening (unlocking) torque in the locked position which is desired to prevent unintended unlocking during distribution or consumer handling that could result in undesired dispensing.

The shroud can include one or more audible emitting ribs. Each rib can engage corresponding grooves. In one example, there can be two pairs grooves built into the actuator body: one for the intended locked and one for the unlocked positions respectively. Each rib can emit a sound both when the actuator is rotated away from/to the locked position or away from/to the unlocked position. Each rib can also cooperate with the grooves to maintain the shroud into the locked or unlocked position respectively.

Shampoo, Conditioner, and Body Wash Compositions

The shampoo, conditioner, and/or body wash composition can be dispensed as a creamy, dense high-quality foam. The foam can appear creamy and conditioning. The foam can have many barely visible bubbles and no large bubbles. The foam can hold its shape and is not generally a runny mess after it is dispensed. The foam can be compliant but can still be easily uniformly spread across the user's hair and/or skin.

The foam shampoo, conditioner, or body wash can be compliant with an elastic modulus from about 10 to about 200 Pa, alternatively from about 15 to about 175 Pa, alternatively from about 20 to about 150 Pa, alternatively from about 25 to about 125 Pa, alternatively from about 30 to about 100 Pa, as determined by the Foam Rheology Method described hereafter.

The foam shampoo can have a stiffness value, a of from about 0.1 to about 0.6, alternatively from about 0.15 to about 0.5, and alternatively from about 0.2 to about 0.4.

Foam Characteristics

A high-quality foam can be dispensed by the aerosol dispenser. The instantaneous foam density can be from about 0.01 g/mL to about to about 0.4 g/mL, alternatively from about 0.03 to about 0.3 g/mL, alternatively from about 0.05 g/mL to about 0.25 g/mL, and alternatively from about 0.07 g/mL to about 0.2 g/mL. The instantaneous foam density can be from about 0.1 g/mL to about 0.4 g/mL, alternatively 0.12 g/mL to about 0.35 g/mL, and alternatively 0.12 g/mL to about 0.25 g/mL. The foam density can be measured by the Instantaneous Foam Density Method, described hereafter.

The compression force can be greater than 6 g, alternatively greater than 10 g, alternatively greater than 14 g. The compression force can be from about 10 g to about 40 g, alternatively from about 13 g to about 36 g, and alternatively from about 14 g to about 33 g. The compression force can be determined by the Foam Compression Test Method, described hereafter.

The dosage of foam can also have a bubble size distribution comprising an $R_{32}$ of from about 5 μm to about 100 μm, alternatively from about 5 μm to about 90 μm, alternatively from about 10 μm to about 60 μm, alternatively from about 20 μm to about 50 ηm, and alternatively from about 25 μm to about 40 μm. the bubble size can be measured by the Kruss Lather Analyzer (Bubble Size) Method, described hereafter.

The dosage of foam can have a yield point of from about 5 Pa to about 100 Pa, alternatively about 10 Pa to about 100 Pa, alternatively from about 20 Pa to about 100 Pa, alternatively from about 25 Pa to about 100 Pa, and alternatively from about 38 Pa to about 100 Pa. The yield point can be measured by the Foam Rheology Method (Yield Point), described hereafter.

Additional description of consumer acceptable foams can be found in U.S. Pub. No. 2018/0110688, incorporated by reference.

Shampoo Composition

The shampoo composition can comprise a cationic deposition polymer, a detersive surfactant, optionally a co-surfactant, an aqueous carrier and optionally additional components such as silicones.

The anhydrous particles when added to the shampoo (which comprise an aqueous phase) become discrete particles. The discrete particles then swell in the aqueous phase. The aqueous phase comprises water and/or suitable solvents. As used herein, the term "suitable solvent" refers to any solvent which can be used in the place of or in combination with water.

Cationic Deposition Polymer

The shampoo compositions may include a cationic deposition polymer. The concentration of the cationic deposition polymer in the shampoo composition can be from about 0.05% to about 5%, alternatively from about 0.075% to about 2.5%, alternatively from about 0.1% to about 1.0%, and alternatively from about 0.5% to about 1.0% by weight of the shampoo composition.

Suitable cationic deposition polymers may have cationic charge densities of at least about 0.4 meq/g, alternatively at least about 0.7 meq/g, alternatively at least about 1.2 meq/g, alternatively at least about 1.5 meq/g, alternatively less than about 7 meq/g, and alternatively less than about 5 meq/g, at the pH of intended use of the composition. The pH will generally range from about pH 3 to about pH 9, alternatively between about pH 4 and about pH 8. The "cationic charge density" of a polymer, as that term is used herein, refers to the ratio of the number of positive charges on the polymer to the molecular weight of the polymer. The weight average molecular weight of such suitable cationic polymers will generally be between about 10,000 and 10 million, alternatively between about 50,000 and about 5 million, and alternatively between about 100,000 and about 3 million.

Suitable cationic polymers for use in the composition include polysaccharide polymers, such as cationic cellulose derivatives and cationic starch derivatives, such as salts of hydroxyethyl cellulose reacted with trimethyl ammonium substituted epoxide. Other suitable cationic polymers include cationic guar gum derivatives, such as guar hydroxypropyltrimonium chloride. Further suitable cationic polymers include galactomannan polymer derivatives having a mannose to galactose ratio of greater than 2:1 on a monomer to monomer basis, such as cassia gum hydroxypropyltrimonium chloride. Particularly suitable cationic deposition polymers include guar hydroxypropyltrimonium chloride.

The cationic guar polymer may be formed from quaternary ammonium compounds. The quaternary ammonium compounds for forming the cationic guar polymer conform to the general formula 1:

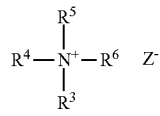

wherein where R3, R4 and R5 are methyl or ethyl groups; R6 is either an epoxyalkyl group of the general formula 2:

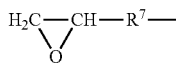

or R6 is a halohydrin group of the general formula 3:

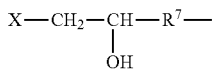

wherein R7 is a C1 to C3 alkylene; X is chlorine or bromine, and Z is an anion such as Cl—, Br—, I— or HSO4-.

The cationic guar polymer can conform to the general formula 4:

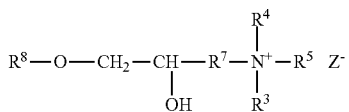

wherein R8 is guar gum; and wherein R4, R5, R6 and R7 are as defined above; and wherein Z is a halogen. The cationic guar polymer can conform to Formula 5:

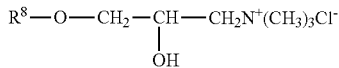

Suitable cationic guar polymers include cationic guar gum derivatives, such as guar hydroxypropyltrimonium chloride. The cationic guar polymer is a guar hydroxypropyltrimonium chloride. Specific examples of guar hydroxypropyltrimonium chlorides include the Jaguar® series commercially available from Rhone-Poulenc Incorporated, for example Jaguar® C-17, which has a cationic charge density of about 0.6 meq/g and a M.Wt. of about 2.2 million g/mol and is available from Rhodia Company. Jaguar® C 13S which has a M.Wt. of 2.2 million g/mol and a cationic charge density of about 0.8 meq/g (available from Rhodia Company). N-Hance 3196, which has a charge density of about 0.7 and a M. Wt. Of about 1,100,000 g/mole and is available from ASI. BF-13, which is a borate (boron) free guar of charge density of about 1.1 meq/g and M. W.t of about 800,000 and BF-17, which is a borate (boron) free guar of charge density of about 1.7 meq/g and M. W.t of about 800,000 both available from ASI.

A combination of cationic polymers can improve the conditioning and lather of the shampoo composition. Using a cationic polymer with a charge density of from about 0.4 meq/g to about 0.8 meq/g, alternatively about 0.7 meq/g in combination with a cationic polymer having a molecular weight greater than about 1,000,000 can result in a shampoo composition with both lather stability and creaminess.

The shampoo composition can comprise a combination of cationic guar and cationic polysaccharide deposition polymers wherein the respective weight ratio of guar to polysaccharide deposition polymers is greater than 2:1, alternatively wherein the weight ratio of guar to polysaccharide deposition polymers is greater than 3:1, and alternatively wherein the weight ratio of guar to polysaccharide deposition polymers is greater than 4:1.

The shampoo composition can comprise a combination of cationic guar polymers only, wherein one cationic guar has a charge density of about 1.7 meq/g and another cationic guar has a molecular weight of about 1,100,000 g/mole.

The shampoo composition can comprise a mixture of 3196 guar and BF-17 cationic guar, wherein the weight ratio of these two cationic deposition polymers is about 5:1, alternatively about 2:1, alternatively about 1:1, still alternatively about 1:2, and alternatively about 2:5 of 3196 to BF-17 respectively.

The shampoo composition can comprise polyquaternium-6, i.e., homopolymer of diallyldimethylammonium chloride.

The polyquaternium-6 can be included in the composition at a level by weight of from about 0.01% to about 5%, alternatively from about 0.03% to about 1%, alternatively from about 0.05% to about 0.5%, and alternatively from about 0.05% to about 0.3%, by weight of the shampoo composition.

The polyquaternium-6 useful herein has a cationic charge density of, from about 3.5 meq/g, alternatively from about 4.5 meq/g, alternatively from about 5.5 meq/g, and alternatively to about 13 meq/g, alternatively to about 10 meq/g, alternatively to about 7.0 meq/g.

The polyquaternium-6 useful herein has a molecular weight of, from about 800 g/mol or more, alternatively from about 1,000 g/mol or more, alternatively from about 1,200 g/mol or more in view of providing improved deposition of metal pyrithione. The molecular weight is also from about 1,000,000 g/mol, alternatively from about 500,000 g/mol, alternatively from about 100,000 g/mol to about 50,000 g/mol.

Commercially available examples of polyquaternium-6 polymer include, for example, that having a tradename Merquat 100 available from Lubrizol, which has a cationic charge density of about 6.19 meq/g, molecular weight of about 150,000 g/mol, and that having a tradename Merquat 106 available from Lubrizol, which has a cationic charge density of about 6.19 meq/g, molecular weight of about 15,000 g/mol.

Detersive Surfactant

The composition can comprise one or more detersive surfactants in the shampoo. The detersive surfactant component can be included in shampoo compositions to provide cleansing performance. The detersive surfactant may be selected from anionic detersive surfactant, zwitterionic, or amphoteric detersive surfactant, or a combination thereof. Such surfactants should be physically and chemically compatible with the components described herein, or should not otherwise unduly impair product stability, aesthetics or performance. Particularly suitable herein is sodium laureth-n-sulfate, wherein n=1 ("SLE1S"). SLE1S enables more efficient lathering and cleaning when compared to higher mole ethoxylate equivalents, especially in a shampoo composition that contains high levels of conditioning actives.

Suitable anionic detersive surfactants include those which are known for use in hair care or other personal care shampoo compositions. The anionic detersive surfactant may be a combination of sodium lauryl sulfate and sodium laureth-n sulfate. The concentration of the anionic surfactant in the composition should be sufficient to provide the desired cleaning and lather performance, and generally range from about 5% to about 50%, alternatively from about 8% to about 30%, alternatively from about 9% to about 25%, and alternatively from about 10% to about 17%, by weight of the composition. Alternatively, the hair care composition may comprise from about 16% to about 40%, alternatively from about 18% to about 36%, alternatively from about 20% to about 32%, alternatively from about 22% to about 28% of one or more anionic surfactants, by weight of the hair care composition.

Suitable zwitterionic or amphoteric detersive surfactants include those which are known for use in hair care or other personal shampoo compositions. Concentration of such amphoteric detersive surfactants range from about 0.5% to about 20%, alternatively from about 1% to about 10%. Non-limiting examples of suitable zwitterionic or amphoteric surfactants are described in U.S. Pat. Nos. 5,104,646 and 5,106,609.

Additional anionic surfactants suitable for use herein include alkyl and alkyl ether sulfates of the formula $ROSO_3M$ and $RO(C_2H_4O)_xSO_3M$, wherein R is alkyl or alkenyl of from about 8 to about 18 carbon atoms, x is 1 to 10, and M is a water-soluble cation such as ammonium, sodium, potassium, and triethanolamine cation or salts of the divalent magnesium ion with two anionic surfactant anions. The alkyl ether sulfates may be made as condensation products of ethylene oxide and monohydric alcohols having from about 8 to about 24 carbon atoms. The alcohols can be derived from fats such as coconut oil, palm oil, palm kernel oil, or tallow, or can be synthetic. Other suitable anionic surfactants include water-soluble salts of the organic, sulfonic acids of the general formula $[R^1—SO_3M]$. $R^1$ being a straight chain aliphatic hydrocarbon radical having from 13 to 17 carbon atoms, alternatively from 13 to 15 carbon atoms. M is a water soluble cation such as ammonium, sodium, potassium, and triethanolamine cation or salts of the divalent magnesium ion with two anionic surfactant anions. These materials are produced by the reaction of $SO_2$ and $O_2$ with suitable chain length normal paraffins ($C_{14}$-$C_{17}$) and are sold commercially as sodium paraffin sulfonates.

Examples of additional anionic surfactants suitable for use include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium trideceth sulfate, sodium tridecyl sulfate, sodium methyl lauroyl taurate, sodium methyl cocoyl taurate, sodium lauroyl isethionate, sodium cocoyl isethionate, sodium laurethsulfosuccinate, sodium laurylsulfosuccinate, sodium tridecyl benzene sulfonate, sodium dodecyl benzene sulfonate, and mixtures thereof.

The shampoo composition may further comprise additional surfactants for use in combination with the anionic detersive surfactant component described herein. Suitable additional surfactants include cationic and nonionic surfactants.

Non-limiting examples of other anionic, zwitterionic, amphoteric, cationic, nonionic, or optional additional surfactants suitable for use in the compositions are described in McCutcheon's, Emulsifiers and Detergents, 1989 Annual, published by M. C. Publishing Co., and U.S. Pat. Nos. 3,929,678; 2,658,072; 2,438,091; and 2,528,378.

The one or more additional anionic surfactants may be selected from the group consisting of isethionates, sarcosinates, sulfonates, sulfosuccinates, sulfoacetates, acyl glycinates, acyl alaninates, acyl glutamates, lactates, lactylates, glucose carboxylates, amphoacetates, taurates, phosphate esters, and mixtures thereof. In that case, alkyl is defined as a saturated or unsaturated, straight or branched alkyl chain with 7 to 17 carbon atoms, alternatively with 9 to 13 carbon atoms. In that case, acyl is defined as of formula R—C(O)—, wherein R is a saturated or unsaturated, straight or branched alkyl chain with 7 to 17 carbon atoms, alternatively with 9 to 13 carbon atoms.

Suitable isethionate surfactants can include the reaction product of fatty acids esterified with isethionic acid and neutralized with sodium hydroxide. Suitable fatty acids for isethionate surfactants can be derived from coconut oil or palm kernel oil including amides of methyl tauride. Non-limiting examples of isethionates can be selected from the group consisting of sodium lauroyl methyl isethionate, sodium cocoyl isethionate, ammonium cocoyl isethionate, sodium hydrogenated cocoyl methyl isethionate, sodium lauroyl isethionate, sodium cocoyl methyl isethionate, sodium myristoyl isethionate, sodium oleoyl isethionate, sodium oleyl methyl isethionate, sodium palm kerneloyl isethionate, sodium stearoyl methyl isethionate, and mixtures thereof.

Non-limiting examples of sarcosinates can be selected from the group consisting of sodium lauroyl sarcosinate, sodium cocoyl sarcosinate, sodium myristoyl sarcosinate, TEA-cocoyl sarcosinate, ammonium cocoyl sarcosinate, ammonium lauroyl sarcosinate, dimer dilinoleyl bis-lauroylglutamate/lauroyl sarcosinate, disodium lauroamphodiacetate, lauroyl sarcosinate, isopropyl lauroyl sarcosinate, potassium cocoyl sarcosinate, potassium lauroyl sarcosinate, sodium cocoyl sarcosinate, sodium lauroyl sarcosinate, sodium myristoyl sarcosinate, sodium oleoyl sarcosinate, sodium palmitoyl sarcosinate, TEA-cocoyl sarcosinate, TEA-lauroyl sarcosinate, TEA-oleoyl sarcosinate, TEA-palm kernel sarcosinate, and combinations thereof.

Non-limiting examples of sulfosuccinate surfactants can include disodium N-octadecyl sulfosuccinate, disodium lauryl sulfosuccinate, diammonium lauryl sulfosuccinate, sodium lauryl sulfosuccinate, disodium laureth sulfosuccinate, tetrasodium N-(1,2-dicarboxyethyl)-N-octadecyl sulfosuccinnate, diamyl ester of sodium sulfosuccinic acid, dihexyl ester of sodium sulfosuccinic acid, dioctyl esters of sodium sulfosuccinic acid, and combinations thereof.

Non-limiting examples of sulfoacetates can include sodium lauryl sulfoacetate, ammonium lauryl sulfoacetate and combination thereof.

Non-limiting examples of acyl glycinates can include sodium cocoyl glycinate, sodium lauroyl glycinate and combination thereof.

Non-limiting example of acyl alaninates can include sodium cocoyl alaninate, sodium lauroyl alaninate, sodium N-dodecanoyl-1-alaninate, and combinations thereof.

Non-limiting examples of acyl glutamates can be selected from the group consisting of sodium cocoyl glutamate, disodium cocoyl glutamate, ammonium cocoyl glutamate, diammonium cocoyl glutamate, sodium lauroyl glutamate, disodium lauroyl glutamate, sodium cocoyl hydrolyzed wheat protein glutamate, disodium cocoyl hydrolyzed wheat protein glutamate, potassium cocoyl glutamate, dipotassium cocoyl glutamate, potassium lauroyl glutamate, dipotassium lauroyl glutamate, potassium cocoyl hydrolyzed wheat protein glutamate, dipotassium cocoyl hydrolyzed wheat protein glutamate, sodium capryloyl glutamate, disodium capryloyl glutamate, potassium capryloyl glutamate, dipotassium capryloyl glutamate, sodium undecylenoyl glutamate, disodium undecylenoyl glutamate, potassium undecylenoyl glutamate, dipotassium undecylenoyl glutamate, disodium hydrogenated tallow glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, sodium cocoyl/hydrogenated tallow glutamate, sodium cocoyl/palmoyl/sunfloweroyl glutamate, sodium hydrogenated tallowoyl glutamate, sodium olivoyl glutamate, disodium olivoyl glutamate, sodium palmoyl glutamate, disodium palmoyl glutamate, TEA-cocoyl glutamate, TEA-hydrogenated tallowoyl glutamate, TEA-lauroyl glutamate, and mixtures thereof.

Non-limiting examples of acyl glycinates can include sodium cocoyl glycinate, sodium lauroyl glycinate and combination thereof.

Non-limiting example of lactates can include sodium lactate.

Non-limiting examples of lactylates can include sodium lauroyl lactylate, sodium cocoyl lactylate and combination thereof.

Non-limiting examples of glucose carboxylates can include sodium lauryl glucoside carboxylate, sodium cocoyl glucoside carboxylate and combinations thereof.

Non-limiting examples of alkylamphoacetates can include sodium cocoyl amphoacetate, sodium lauroyl amphoacetate and combination thereof.

Non-limiting examples of acyl taurates can include sodium methyl cocoyl taurate, sodium methyl lauroyl taurate, sodium methyl oleoyl taurate and combination thereof.

Co-Surfactant

Co-surfactants are materials which are combined with the undecyl sulfate surfactant and optionally anionic surfactants to enhance lather volume and/or to modify lather texture. Typically these materials can be selected from a variety of families of structures including, but not limited to, amphoteric, zwitterionic, cationic, and nonionic. They are typically used with anionic surfactants in a weight ratio of 1:20 to 1:4, and alternatively in the 1:12 to 1:7 weight ratio.

The shampoo composition may comprise from about 0.5 wt % to about 10 wt %, alternatively from about 0.5 wt % to about 5 wt %, alternatively from about 0.5 wt % to about 3 wt %, alternatively from about 0.5 wt % to about 2 wt %, and alternatively from about 0.5 wt % to about 1.75 wt % by weight of the composition of at least one suitable co-surfactant. Alternatively, the hair composition may comprise from about 0.25% to about 14%, alternatively from about 1% to about 12%, alternatively from about 3% to about 10%, alternatively from about 4% to about 9% of one or more co-surfactants, by weight of the hair care composition.

The co-surfactant may serve to produce faster lather, facilitate easier rinsing, and/or mitigate harshness on the keratinous tissue. The co-surfactant further may aid in producing lather having more desirable texture, volume and/or other properties.

Amphoteric surfactants suitable for use herein include, but are not limited to derivatives of aliphatic secondary and tertiary amines in which the aliphatic radical can be straight or branched chain and wherein one substituent of the aliphatic substituents contains from about 8 to about 18 carbon atoms and one contains an anionic water solubilizing group, e.g., carboxy, sulfonate, sulfate, phosphate, or phosphonate. Examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378, and mixtures thereof. The amphoteric surfactants may selected from the family of betaines such as lauryolamphoacetate.

Zwitterionic surfactants suitable for use herein include, but are not limited to derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Other zwitterionic surfactants suitable for use herein include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. The sulfobetaines may include coco dimethyl sulfopropyl betaine, stearyl dimethyl sulfopropyl betaine, lauryl dimethyl sulfoethyl betaine, lauryl bis-(2-hydroxyethyl) sulfopropyl betaine and mixtures thereof. Other suitable amphoteric surfactants include amidobetaines and amidosulfobetaines, wherein the RCONH $(CH_2)_3$ radical, wherein R is a $C_{11}$-$C_{17}$ alkyl, is attached to the nitrogen atom of the betaine.

Nonionic co-surfactants suitable for use in the composition for enhancing lather volume or texture include water soluble materials like lauryl dimethylamine oxide, cocodimethylamine oxide, cocoamidopropylamine oxide, laurylamidopropyl amine oxide, etc. or alkylpolyethoxylates like laureth-4 to laureth-7 and water insoluble components such as cocomonoethanol amide, cocodiethanol amide, lauroylmonoethanol amide, alkanoyl isopropanol amides, and fatty alcohols like cetyl alcohol and oleyl alcohol, and 2-hydroxyalkyl methyl ethers, etc.

Further suitable materials as co-surfactants herein include 1,2-alkylepoxides, 1,2-alkanediols, branched or straight chain alkyl glyceryl ethers (e.g., as disclosed in EP 1696023A1), 1,2-alkylcyclic carbonates, and 1,2-alkyl cyclicsulfites, particularly those wherein the alkyl group contains 6 to 14 carbon atoms in linear or branched configuration. Other examples include the alkyl ether alcohols derived from reacting $C_{10}$ or $C_{12}$ alpha olefins with ethylene glycol (e.g., hydroxyethyl-2-decyl ether, hydroxyethyl-2-dodecyl ether), as can be made according to U.S. Pat. Nos. 5,741,948; 5,994,595; 6,346,509; and 6,417,408.

Other nonionic surfactants may be selected from the group consisting of glucose amides, alkyl polyglucosides, sucrose cocoate, sucrose laurate, alkanolamides, ethoxylated alcohols and mixtures thereof. The nonionic surfactant is selected from the group consisting of glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

The co-surfactant can be selected from the group consisting of Cocomonoethanol Amide, Cocoamidopropyl Betaine, Laurylamidopropyl Betaine, Cocobetaine, lauryl betaine, lauryl amine oxide, sodium lauryl amphoacetate; alkyl glyceryl ethers, alkyl-di-glyceryl ethers, 1,2-alkyl cyclic sulfites, 1,2-alkyl cyclic carbonates, 1,2-alkyl-epoxides, alkyl glycidylethers, and alkyl-1,3-dioxolanes, wherein the alkyl group contains 6 to 14 carbon atoms in linear or branched configuration; 1,2-alkane diols where the total carbon content is from 6 to 14 carbon atoms linear or branched, methyl-2-hydroxy-decyl ethers, hydroxyethyl-2-dodecyl ether, hydroxyethyl-2-decyl ether, and mixtures thereof.

Cationic surfactants may be derived from amines that are protonated at the pH of the formulation, e.g. bis-hydroxyethyl lauryl amine, lauryl dimethylamine, lauroyl dimethyl amidoproplyl amine, cocoylamidopropyl amine, and the like. The cationic surfactants may also be derived from fatty quaternary ammonium salts such as lauryl trimethylammonium chloride and lauroylamidopropyl trimethyl ammonium chloride.

Alkylamphoacetates are suitable surfactants used in the compositions herein for improved product mildness and lather. The most commonly used alkylamphoacetates are lauroamphoacetate and cocoamphoacetate. Alkylamphoacetates can be comprised of monoacetates and diacetates. In some types of alkylamphoacetates, diacetates are impurities or unintended reaction products. However, the presence of diacetate can cause a variety of unfavorable composition characteristics when present in amounts over 15% of the alkylamphoacetates.

Suitable nonionic surfactants for use herein are those selected from the group consisting of glucose amides, alkyl polyglucosides, sucrose cocoate, sucrose laurate, alkanolamides, ethoxylated alcohols and mixtures thereof. In one embodiment the nonionic surfactant is selected from the group consisting of glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

Non-limiting examples of suitable structurants are described in U.S. Pat. No. 5,952,286, and include unsaturated and/or branched long chain ($C_8$-$C_{24}$) liquid fatty acids or ester derivative thereof; unsaturated and/or branched long chain liquid alcohol or ether derivatives thereof, and mixtures thereof. The surfactant also may comprise short chain saturated fatty acids such as capric acid and caprylic acid. Without being limited by theory, it is believed that the unsaturated part of the fatty acid of alcohol or the branched part of the fatty acid or alcohol acts to "disorder" the surfactant hydrophobic chains and induce formation of lamellar phase. Examples of suitable liquid fatty acids include oleic acid, isostearic acid, linoleic acid, linolenic acid, ricinoleic acid, elaidic acid, arichidonic acid, myristoleic acid, palmitoleic acid, and mixtures thereof. Examples of suitable ester derivatives include propylene glycol isostearate, propylene glycol oleate, glyceryl isostearate, glyceryl oleate, polyglyceryl diisostearate and mixtures thereof. Examples of alcohols include oleyl alcohol and isostearyl alcohol. Examples of ether derivatives include isosteareth or oleth carboxylic acid; or isosteareth or oleth alcohol. The structuring agent may be defined as having melting point below about 25° C.

If present, the composition may comprise a rheology modifier, wherein said rheology modifier comprises cellulosic rheology modifiers, cross-linked acrylates, cross-linked maleic anhydride co-methylvinylethers, hydrophobically modified associative polymers, or a mixture thereof.

An electrolyte, if used, can be added per se to the composition or it can be formed in situ via the counterions included in one of the raw materials. The electrolyte may include an anion comprising phosphate, chloride, sulfate or citrate and a cation comprising sodium, ammonium, potassium, magnesium or mixtures thereof. The electrolyte may be sodium chloride, ammonium chloride, sodium or ammonium sulfate. The electrolyte may be added to the composition in the amount of from about 0.1 wt % to about 15 wt % by weight, alternatively from about 1 wt % to about 6 wt % by weight, and alternatively from about 3 wt % to about 6 wt %, by weight of the composition.

Aqueous Carrier

The shampoo compositions may comprise an aqueous carrier. Typically, the compositions are in the form of pourable liquids (under ambient conditions). The compositions, therefore, comprise an aqueous carrier at a level of at least about, alternatively from about 20% to about 95%, and alternatively from about 60% to about 85%, by weight of the compositions. The aqueous carrier may comprise water, or a miscible mixture of water and organic solvent. The aqueous carrier may also comprise water with minimal or no significant concentrations of organic solvent, except as otherwise incidentally incorporated into the composition as minor ingredients of other components.

Additional Components

The shampoo compositions may further comprise one or more optional components known for use in hair care or personal care products, provided that the optional components are physically and chemically compatible with the components described herein, or do not otherwise unduly impair product stability, aesthetics or performance Individual concentrations of such optional components may range from about 0.001% to about 10% by weight of the compositions.

Non-limiting examples of optional components for use in the composition include cationic polymers, conditioning agents (hydrocarbon oils, fatty esters, silicones), anti-dandruff agents, suspending agents, viscosity modifiers, dyes, nonvolatile solvents or diluents (water soluble and insoluble), pearlescent aids, foam boosters, additional surfactants or nonionic co-surfactants, pediculocides, pH adjusting agents, perfumes, preservatives, chelants, proteins, skin active agents, sunscreens, UV absorbers, and vitamins.

Conditioner Composition

The conditioner composition can contain a cationic surfactant, high melting point fatty compounds, an aqueous carrier (as described above), and optionally conditioning agents (as described above) including silicone compounds (as described hereafter).

In the conditioner compositions, a gel matrix can be present. The gel matrix can be formed by the cationic surfactant, the high melting point fatty compound, and the aqueous carrier. When the gel matrix is formed, the composition can be substantially free of anionic surfactants, in view of stability of the gel matrix. As used herein, "the composition being substantially free of anionic surfactants" means that: the composition is free of anionic surfactants; or, if the composition contains anionic surfactants, the level of such anionic surfactants is very low. In the conditioner compositions the total level of such anionic surfactants, if included, can be 1% or less, alternatively 0.5% or less, alternatively 0.1% or less by weight of the composition. The total level of such anionic surfactants can 0% by weight of the composition.

In some examples, the conditioner composition can be free of high melting point fatty compounds and may not contain a gel matrix.

Cationic Surfactant

The conditioner compositions can include cationic surfactant. The cationic surfactant can be included in the composition at a level of from about 0.1% to about 20.0%, alternatively from about 0.5% to about 10.0%, alternatively from about 0.8% to about 8.0%, alternatively from about 1.0% to about 6.0%, alternatively from about 1% to about 3%, by weight of the composition.

The surfactant can be water-insoluble. As used herein, "water-insoluble surfactants" means that the surfactants have a solubility in water at 25° C. of below 0.5 g/100 g (excluding 0.5 g/100 g) water, alternatively 0.3 g/100 g water or less.

Cationic surfactant useful herein can be one cationic surfactant or a mixture of two or more cationic surfactants. The cationic surfactant can be selected from: a mono-long alkyl quaternized ammonium salt; a combination of a mono-long alkyl quaternized ammonium salt and a di-long alkyl quaternized ammonium salt; a mono-long alkyl amine; a combination of a mono-long alkyl amine and a di-long alkyl quaternized ammonium salt; and a combination of a mono-long alkyl amine and a mono-long alkyl quaternized ammonium salt.

Mono-Long Alkyl Amine

Mono-long alkyl amine useful herein are those having one long alkyl chain of from 12 to 30 carbon atoms, alternatively from 16 to 24 carbon atoms, and alternatively from 18 to 22 alkyl group. Mono-long alkyl amines useful herein also include mono-long alkyl amidoamines Primary, secondary, and tertiary fatty amines are useful.

Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethyl amine, palmitamidopropyldiethylamine, palmitamidoethyldiethyl amine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethyl amine, arachidamidoethyldiethylamine, arachidamidoethyldimethylamine, diethylaminoethylstearamide. Useful amines in the present invention are disclosed in U.S. Pat. No. 4,275,055, Nachtigal, et al.

These amines are used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; alternatively l-glutamic acid, lactic acid, citric acid, at a molar ratio of the amine to the acid of from about 1:0.3 to about 1:2, more alternatively from about 1:0.4 to about 1:1.

Mono-Long Alkyl Quaternized Ammonium Salt

The mono-long alkyl quaternized ammonium salts useful herein are those having one long alkyl chain which has from 12 to 30 carbon atoms, alternatively from 16 to 24 carbon atoms, alternatively C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

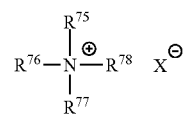

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. One of $R^{75}$, $R^{76}$, $R^{77}$ and $R^{78}$ can be selected from an alkyl group of from 12 to 30 carbon atoms, alternatively from 16 to 24 carbon atoms, alternatively from 18 to 22 carbon atoms, alternatively 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Di-Long Alkyl Quaternized Ammonium Salts

When used, di-long alkyl quaternized ammonium salts can be combined with a mono-long alkyl quaternized ammonium salt and/or mono-long alkyl amine salt, at the weight ratio of from 1:1 to 1:5, alternatively from 1:1.2 to 1:5, and alternatively from 1:1.5 to 1:4, in view of stability in rheology and conditioning benefits.

Di-long alkyl quaternized ammonium salts useful herein are those having two long alkyl chains of from 12 to 30 carbon atoms, alternatively from 16 to 24 carbon atoms, and alternatively from 18 to 22 carbon atoms. Such di-long alkyl quaternized ammonium salts useful herein are those having the formula (I):

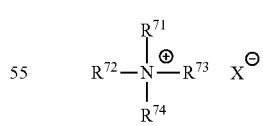

wherein two of $R^{71}$, $R^{72}$, $R^{73}$ and $R^{74}$ are selected from an aliphatic group of from 12 to 30 carbon atoms, alternatively from 16 to 24 carbon atoms, and alternatively from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, alternatively from 1 to 3 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Two of $R^{71}$, $R^{72}$, $R^{73}$ and $R^{74}$ can be selected from an alkyl group of from 12 to 30 carbon atoms, alternatively from 16 to 24 carbon atoms, and alternatively from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Di-long alkyl cationic surfactants can include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

High Melting Point Fatty Compound

The composition of the present invention can contain a high melting point fatty compound. The high melting point fatty compound can be included in the composition at a level of from about 1 the hair care composition may comprise from about 0% to about 8% fatty alcohols, alternatively from about 0.5% to about 6%, alternatively from about 1.0% to about 4%, and alternatively from about 1.5% to about 3.0%, by weight of the composition. The condition may comprise less than 10% high melting point fatty compounds, alternatively less than 8% high melting point fatty compounds, alternatively less than 6% high melting point fatty compounds, alternatively less than 3% high melting point fatty compound, alternatively may be substantially free of high melting point fatty compounds, and alternatively may comprise 0% high melting point fatty compounds, by weight of the concentrated hair care composition.

The high melting point fatty compound useful herein can have a melting point of 25° C. or higher, alternatively 40° C. or higher, alternatively 45° C. or higher, alternatively 50° C. or higher, in view of stability of the emulsion especially the gel matrix. Such melting point can be up to about 90° C., alternatively up to about 80° C., alternatively up to about 70° C., alternatively up to about 65° C., in view of easier manufacturing and easier emulsification. The high melting point fatty compound can be used as a single compound or as a blend or mixture of at least two high melting point fatty compounds. When used as such blend or mixture, the above melting point means the melting point of the blend or mixture.

The high melting point fatty compound useful herein can be selected from the group consisting of fatty alcohols, fatty acids, and mixtures thereof. Further, it is understood by the artisan that, depending on the number and position of double bonds, and length and position of the branches, certain compounds having certain required carbon atoms may have a melting point of less than the above preferred in the present invention. Such compounds of low melting point are not intended to be included in this section. Nonlimiting examples of the high melting point compounds can be found in International Cosmetic Ingredient Dictionary, Fifth Edition, 1993, and CTFA Cosmetic Ingredient Handbook, Second Edition, 1992.

Among a variety of high melting point fatty compounds, fatty alcohols can be used in the composition of the present invention. The fatty alcohols useful herein are those having from about 14 to about 30 carbon atoms, and alternatively from about 16 to about 22 carbon atoms. These fatty alcohols can be saturated and can be straight or branched chain alcohols.

Fatty alcohols can include, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group.

The fatty alcohol can be a mixture of cetyl alcohol and stearyl alcohol.

Generally, in the mixture, the weight ratio of cetyl alcohol to stearyl alcohol can be from about 1:9 to 9:1, alternatively from about 1:4 to about 4:1, and alternatively from about 1:2.3 to about 1.5:1.

When using higher level of total cationic surfactant and high melting point fatty compounds, the mixture can have the weight ratio of cetyl alcohol to stearyl alcohol of alternatively from about 1:1 to about 4:1, alternatively from about 1:1 to about 2:1, alternatively from about 1.2:1 to about 2:1, in view of avoiding to get too thick for spreadability. It may also provide more conditioning on damaged part of the hair.

Silicone Compound

The compositions of the present invention may comprise a silicone compound. The silicone compound can be contained in the composition at a level of from about 0.05% to about 15%, alternatively from about 0.1% to about 10%, alternatively from about 0.15% to about 5%, and alternatively from about 1% to about 6% by weight of the composition.

Silicone Polymer Containing Quaternary Ammonium Groups

Such silicone compounds useful herein may be those having an amine or a quaternary ammonium group; and an alkylene oxide group, for example, Trideceth-9-amodimethicone, Silicone Quaternium-22. and those described below in detail.

Silicone compounds useful herein include, for example, a Silicone Polymer Containing Quaternary Groups comprising terminal ester groups, having a viscosity up to 100,000 mPa·s and a D block length of greater than 200 D units. Without being bound by theory, this low viscosity silicone polymer provides improved conditioning benefits, for example, hair conditioning benefits such as smooth feel, reduced friction, and prevention of hair damage, while eliminating the need for a silicone blend.

Structurally, the silicone polymer is a polyorganosiloxane compound comprising one or more quaternary ammonium groups, at least one silicone block comprising greater than 200 siloxane units, at least one polyalkylene oxide structural unit, and at least one terminal ester group. In one or more embodiments, the silicone block may comprise between 300 to 500 siloxane units.

The polyorganosiloxane compounds can have the general formulas (Ia) and (Ib):

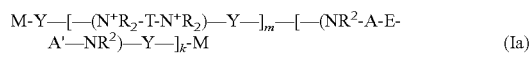

(Ia)

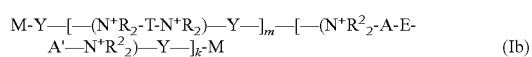

(Ib)

wherein:

m can be >0, alternatively 0.01 to 100, alternatively 0.1 to 100, alternatively 1 to 100, alternatively 1 to 50, alternatively 1 to 20, alternatively 1 to 10, k is 0 or an average value of from >0 to 50, alternatively from 1 to 20, or alternatively from 1 to 10, M represents a terminal group, comprising terminal ester groups selected from

—OC(O)—Z
—OS(O)$_2$—Z
—OS(O$_2$O—Z
—OP(O)O—Z)OH
—OP(O)(O—Z)$_2$ wherein Z is selected from monovalent organic residues having up to 40 carbon atoms, optionally comprising one or more hetero atoms.

A and A' each are independently from each other selected from a single bond or a divalent organic group having up to 10 carbon atoms and one or more hetero atoms, and E is a polyalkylene oxide group of the general formula:

—[CH$_2$CH$_2$O]$_q$—[CH$_2$CH(CH$_3$)O]$_r$—[CH$_2$CH(C$_2$H$_5$)O]$_s$— wherein q=0 to 200, r=0 to 200, s=0 to 200, and q+r+s=1 to 600.

R$^2$ is selected from hydrogen or R,

R is selected from monovalent organic groups having up to 22 carbon atoms and optionally one or more heteroatoms, and wherein the free valencies at the nitrogen atoms are bound to carbon atoms, Y is a group of the formula:

—K—S—K— and -A-E-A'- or -A'-E-A-,

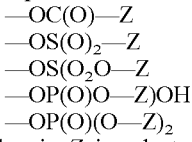

with S= wherein R1=C$_1$-C$_{22}$-alkyl, C$_1$-C$_{22}$-fluoralkyl or aryl; n=200 to 1000, and these can be identical or different if several S Groups are present in the polyorganosiloxane compound.

K is a bivalent or trivalent straight chain, cyclic and/or branched C$_2$-C$_{40}$ hydrocarbon residue which is optionally interrupted by —O—, —NH—, trivalent N, —NR$^1$—, —C(O)—, —C(S)—, and optionally substituted with —OH, wherein R$^1$ is defined as above, T is selected from a divalent organic group having up to 20 carbon atoms and one or more hetero atoms.

The residues K may be identical or different from each other. In the —K—S—K-moiety, the residue K is bound to the silicon atom of the residue S via a C—Si-bond.

Due to the possible presence of amine groups (—(NR$^2$-A-E-A'—NR$^2$)—) in the polyorganosiloxane compounds, they may have protonated ammonium groups, resulting from the protonation of such amine groups with organic or inorganic acids. Such compounds are sometimes referred to as acid addition salts of the polyorganosiloxane compounds.

The molar ratio of the quaternary ammonium groups b) and the terminal ester groups c) can be less than 100:20, alternatively less than 100:30 and alternatively less than 100:50. The ratio can be determined by $^{13}$C-NMR.

In a further embodiment, the polyorganosiloxane composition may comprise:

A) at least one polyorganosiloxane compound, comprising a) at least one polyorganosiloxane group, b) at least one quaternary ammonium group, c) at least one terminal ester group, and d) at least one polyalkylene oxide group (as defined before), B) at least one polyorganosiloxane compound, comprising at least one terminal ester group, different from compound A).

In the definition of component A) it can be referred to the description of the polyorganosiloxane compounds of the invention. The polyorganosiloxane compound B) can differ from the polyorganosiloxane compound A) in that it does not comprise quaternary ammonium groups. Polyorganosiloxane compounds B) can result from the reaction of monofunctional organic acids, in particular carboxylic acids, and polyorganosiloxane containing bisepoxides.

In the polyorganosiloxane compositions the weight ratio of compound A) to compound B) can be less than 90:10. Or in other words, the content of component B) can be at least 10 weight percent. In one example of the polyorganosiloxane compositions in compound A) the molar ratio of the quaternary ammonium groups b) and the terminal ester groups c) can be less than 100:10, alternatively less than 100:15 and alternatively less than 100:20.

The silicone polymer has a viscosity at 20° C. and a shear rate of 0.1 s$^{-1}$ (plate-plate system, plate diameter 40 mm, gap width 0.5 mm) of less than 100,000 mPa·s (100 Pa·s). In further embodiments, the viscosities of the neat silicone polymers may range from 500 to 100,000 mPa·s, or alternatively from 500 to 70,000 mPa·s, or alternatively from 500 to 50,000 mPa·s, or alternatively from 500 to 20,000 mPa·s. In further embodiments, the viscosities of the neat polymers may range from 500 to 10,000 mPa·s, alternatively 500 to 5000 mPa·s determined at 20° C. and a shear rate of 0.1 s$^{-1}$.

In addition to the above listed silicone polymers, the following preferred compositions are provided below. For example, in the polyalkylene oxide group E of the general formula:

—[CH$_2$CH$_2$O]$_q$—[CH$_2$CH(CH$_3$)O]$_r$—[CH$_2$CH(C$_2$H$_5$)O]$_s$— wherein the q, r, and s indices may be defined as follows:
q=0 to 200, alternatively from 0 to 100, alternatively from 0 to 50, or alternatively from 0 to 20, r=0 to 200, or alternatively from 0 to 100, or alternatively from 0 to 50, or alternatively from 0 to 20,
s=0 to 200, or alternatively from 0 to 100, or alternatively from 0 to 50, or alternatively from 0 to 20,
and q+r+s=1 to 600, or alternatively from 1 to 100, or alternatively from 1 to 50, or alternatively from 1 to 40.

For polyorganosiloxane structural units with the general formula S:

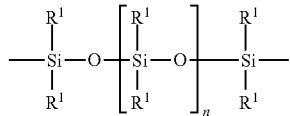

R$^1$=C$_1$-C$_{22}$-alkyl, C$_1$-C$_{22}$-fluoralkyl or aryl; n=from 200 to 1000, or preferably from 300 to 500, K (in the group —K—S—K—) can be a bivalent or trivalent straight chain, cyclical or branched C$_2$-C$_{20}$ hydrocarbon residue which is optionally interrupted by —O—, —NH—, trivalent N, —NR$^1$—, —C(O)—, —C(S)—, and optionally substituted with —OH.

In specific examples, $R^1$ is $C_1$-$C_{18}$ alkyl, $C_1$-$C_{18}$ fluoroalkyl and aryl. Furthermore, $R^1$ is preferably $C_1$-$C_{18}$ alkyl, $C_1$-$C_6$ fluoroalkyl and aryl. Furthermore, $R^1$ can be $C_1$-$C_6$ alkyl, $C_1$-$C_6$ fluoroalkyl, alternatively $C_1$-$C_4$ fluoroalkyl, and phenyl. IV can be methyl, ethyl, trifluoropropyl and/or phenyl.

As used herein, the term "$C_1$-$C_{22}$ alkyl" means that the aliphatic hydrocarbon groups possess from 1 to 22 carbon atoms which can be straight chain or branched. Methyl, ethyl, propyl, n-butyl, pentyl, hexyl, heptyl, nonyl, decyl, undecyl, isopropyl, neopentyl and 1,2,3-trimethyl hexyl moieties serve as examples.

Further as used herein, the term "$C_1$-$C_{22}$ fluoroalkyl" means aliphatic hydrocarbon compounds with 1 to 22 carbon atoms which can be straight chain or branched and are substituted with at least one fluorine atom. Monofluormethyl, monofluoroethyl, 1,1,1-trifluorethyl, perfluoroethyl, 1,1,1-trifluoropropyl, 1,2,2-trifluorobutyl are suitable examples.

Moreover, the term "aryl" means unsubstituted or phenyl substituted once or several times with OH, F, Cl, $CF_3$, $C_1$-$C_6$ alkyl, $C_1$-$C_6$ alkoxy, $C_3$-$C_7$ cycloalkyl, $C_2$-$C_6$ alkenyl or phenyl. Aryl may also mean naphthyl.

For the embodiments of the polyorganosiloxanes, the positive charges resulting from the ammonium group(s), are neutralized with inorganic anions such as chloride, bromide, hydrogen sulfate, sulfate, or organic anions, like carboxylates deriving from $C_1$-$C_{30}$ carboxylic acids, for example acetate, propionate, octanoate, especially from $C_{10}$-$C_{18}$ carboxylic acids, for example decanoate, dodecanoate, tetradecanoate, hexadecanoate, octadecanoate and oleate, alkylpolyethercarboxylate, alkylsulphonate, arylsulphonate, alkylarylsulphonate, alkylsulphate, alkylpolyethersulphate, phosphates derived from phosphoric acid mono alkyl/aryl ester and phosphoric acid dialkyl/aryl ester. The properties of the polyorganosiloxane compounds can be, inter alia, modified based upon the selection of acids used.

The quaternary ammonium groups are usually generated by reacting the di-tertiary amines with an alkylating agents, selected from in particular di-epoxides (sometimes referred to also as bis-epoxides) in the presence of mono carboxylic acids and difunctional dihalogen alkyl compounds.

In one example, the polyorganosiloxane compounds can be of the general formulas (Ia) and (Ib):

M-Y—[—(N⁺R$_2$-T-N⁺R$_2$)—Y—]$_m$—[—(NR²-A-E-A'—NR²)—Y—]$_k$-M    (Ia)

M-Y—[—(N⁺R$_2$-T-N⁺R$_2$)—Y—]$_m$—[—(N⁺R²$_2$-A-E-A'—N⁺R²$_2$)—Y—]$_k$-M    (Ib)

wherein each group is as defined above; however, the repeating units are in a statistical arrangement (i.e., not a block-wise arrangement).

In another example, the polyorganosiloxane compounds may be also of the general formulas (IIa) or (IIb):

M-Y—[—N⁺R$_2$—Y—]$_m$—[—(NR²-A-E-A'—NR²)—Y—]$_k$-M    (IIa)

M-Y—[—N⁺R$_2$—Y—]$_m$—[—(N⁺R²$_s$-A-E-A'—N⁺R²$_2$)—Y—]$_k$-M    (IIb)

wherein each group is as defined above. Also in such formula the repeating units are usually in a statistical arrangement (i.e not a block-wise arrangement).
wherein, as defined above, M is

—OC(O)—Z,

—OS(O)$_2$—Z

—OS(O$_2$)O—Z

—OP(O)(O—Z)OH

—OP(O)(O—Z)$_2$

Z is a straight chain, cyclic or branched saturated or unsaturated $C_1$-$C_{20}$, or alternatively $C_2$ to $C_{18}$, or alternatively a hydrocarbon radical, which can be interrupted by one or more —O—, or —C(O)— and substituted with —OH. In a specific embodiment, M is —OC(O)—Z resulting from normal carboxylic acids in particular with more than 10 carbon atoms like for example dodecanoic acid.

In a further embodiment, the molar ratio of the polyorganosiloxane-containing repeating group —K—S—K— and the polyalkylene repeating group -A-E-A'— or -A'-E-A- is between 100:1 and 1:100, or alternatively between 20:1 and 1:20, or alternatively between 10:1 and 1:10.

In the group —(N⁺R$_2$-T-N⁺R$_2$)—, R may represent a monovalent straight chain, cyclic or branched $C_1$-$C_{20}$ hydrocarbon radical, which can be interrupted by one or more —O—, —C(O)— and can be substituted by —OH, T may represent a divalent straight-chain, cyclic, or branched $C_1$-$C_{20}$ hydrocarbon radical, which can be interrupted by —O—, —C(O)— and can be substituted by hydroxyl.

The above described polyorganosiloxane compounds comprising quaternary ammonium functions and ester functions may also contain: 1) individual molecules which contain quaternary ammonium functions and no ester functions; 2) molecules which contain quaternary ammonium functions and ester functions; and 3) molecules which contain ester functions and no quaternary ammonium functions. While not limited to structure, the above described polyorganosiloxane compounds comprising quaternary ammonium functions and ester functions are to be understood as mixtures of molecules comprising a certain averaged amount and ratio of both moieties.

Various monofunctional organic acids may be utilized to yield the esters. Exemplary embodiments include $C_1$-$C_{30}$ carboxylic acids, for example $C_2$, $C_3$, $C_8$ acids, $C_{10}$-$C_{18}$ carboxylic acids, for example $C_{12}$, $C_{14}$, $C_{16}$ acids, saturated, unsaturated and hydroxyl functionalized $C_{18}$ acids, alkylpolyethercarboxylic acids, alkylsulphonic acids, arylsulphonic acids, alkylarylsulphonic acids, alkylsulphuric acids, alkylpolyethersulphuric acids, phosphoric acid mono alkyl/aryl esters and phosphoric acid dialkyl/aryl esters.

Other Silicones

Such other silicones useful herein can be, for example, volatile silicones such as cyclic silicones, dimethylpolysiloxane fluid, dimethylpolysiloxane gum, amino silicone, and silicone copolyol. Aminosilicones can include, for example, those which conform to the general formula (I):

(R$_1$)$_a$G$_{3-a}$-Si—(—OSiG$_2$)$_n$-(—OSiG$_b$(R$_1$)$_{2-b}$)$_m$—O—SiG$_{3-a}$(R$_1$)$_a$ wherein G is hydrogen, phenyl, hydroxy, or $C_1$-$C_8$ alkyl, alternatively methyl; a is 0 or an integer having a value from 1 to 3, alternatively 1; b is 0, 1 or 2, alternatively 1; n is a number from 0 to 1,999; m is an integer from 0 to 1,999; the sum of n and m is a number from 1 to 2,000; a and m are not both 0; $R_1$ is a monovalent radical conforming to the general formula $C_qH_{2q}L$, wherein q is an integer having a value from 2 to 8 and L is selected from the following groups: —N(R$_2$)CH$_2$—CH$_2$—N(R$_2$)$_2$; —(R$_2$)$_2$; —N(R$_2$)$_3$A⁻; —N(R$_2$CH$_2$—CH$_2$—NR$_2$H$_2$A⁻; wherein R$_2$ is hydrogen, phenyl, benzyl, or a saturated hydrocarbon radical, alternatively an alkyl radical from about $C_1$ to about $C_{20}$; A⁻ is a halide ion.

Amino silicones can include corresponding to formula (I) wherein m=0, a=1, q=3, G=methyl, n can be from about 1500 to about 1700, alternatively about 1600; and L is —N(CH$_3$)$_2$ or —NH$_2$, alternatively —NH$_2$. Alternatively, amino silicones can include those corresponding to formula (I) wherein m=0, a=1, q=3, G=methyl, n can be from about 400 to about 600, alternatively about 500; and L is —N(CH$_3$)$_2$ or —NH$_2$, alternatively —NH$_2$. Amino silicones can be called as terminal aminosilicones, as one or both ends of the silicone chain are terminated by nitrogen containing group.

Propellant

The composition described herein may comprise from about from about 2% to about 10% propellant, also referred to as blooming agent, alternatively from about 3% to about 8% propellant, and alternatively from about 4% to about 7% propellant, by weight of the composition.

The propellant may comprise one or more volatile materials, which in a gaseous state, may carry the other components of the composition in particulate or droplet form. The propellant may have a boiling point within the range of from about −45° C. to about 5° C. The propellant may be liquefied when packaged in convention aerosol containers under pressure. The rapid boiling of the propellant upon leaving the aerosol foam dispenser may aid in the atomization of the other components of the composition.

Aerosol propellants which may be employed in the aerosol composition may include the chemically-inert hydrocarbons such as propane, n-butane, isobutane, cyclopropane, and mixtures thereof, as well as halogenated hydrocarbons such as dichlorodifluoromethane, 1,1-dichloro-1,1,2,2-tetrafluoroethane, 1-chloro-1,1-difluoro-2,2-trifluoroethane, 1-chloro-1,1-difluoroethylene, 1,1-difluoroethane, dimethyl ether, monochlorodifluoromethane, trans-1-chloro-3,3,3-trifluoropropene, trans-1,3,3,3-tetrafluoropropene (HFO 1234ze available by Honeywell), and mixtures thereof. The propellant may comprise hydrocarbons such as isobutane, propane, and butane—these materials may be used for their low ozone reactivity and may be used as individual components where their vapor pressures at 21.1° C. range from about 1.17 Bar to about 7.45 Bar, alternatively from about 1.17 Bar to about 4.83 Bar, and alternatively from about 2.14 Bar to about 3.79 Bar. The propellant may comprise an Isobutane/Propane blend, such as A46 from Aeropres Corp (Hillsborough US). The propellant may comprise hydrofluoroolefins (HFOs).

TEST METHODS

Foam Compression

To measure the compressibility of the foam dispensed by the composition, a Texture Analyzer TA-XT Plus C (Stable Micro Systems Ltd, Surrey, UK) is used equipped with a 5 kg load cell and a disk probe having 1-inch diameter and 0.25 inches height at ambient conditions. The foam produced by the composition is dispensed into a cup (inner diameter 1.5 inches 1 inch deep) and the excess foam is removed so that the foam surface is smoothed with a spatula. The probe zero point is at the foam top surface. The probe is inserted into the foam sample using 2 gram-force. Data are collected for both force and distance. Compressive force (g) is measured at a compression rate of 2 mm/sec over a depth of 19 mm. The measurements are repeated at least three times and averaged. To determine the compressibility of the foam, the maximum observed force (g) is reported at the compression depth of 19 mm.

Instantaneous Foam Density

Foam density is measured by placing a 100 mL beaker onto a mass balance, tarring the mass of the beaker and then dispensing product from the aerosol container into the 100 ml beaker until the volume of the foam is above the rim of the vessel. The foam is made level with the top of the beaker by scraping a spatula across it within 10 seconds of dispensing the foam above the rim of the vessel. The resulting mass of the 100 mL of foam is then divided by the volume (100) to determine the foam density in units of g/ml.

Method of Measuring Foam Volume

Foam volume is measured by placing a weigh boat onto a mass balance, tarring the mass of the weigh boat and then dispensing the desired amount of product from the aerosol container. The grams of foam dispensed is determined and then divided by the density of foam as determined from the Foam Density methodology to reach a volume of foam in mL or cm$^3$.

Foam Rheology Method (Elastic Modulus and Yield Point)

Dynamic oscillation stress sweep is performed to determine the elastic modulus (G') and yield point. The foam is applied to the AR1000 rheometer (available from TA Instruments, New Castle, Del., United States) for oscillation stress sweep. 60 mm smooth acrylic plate is utilized for shear stress measurement. Measurement is made at 25° C. The plate head is lowered to 1200 microns and excess foam is removed with a spatula so that drag does not occur during measurement. The measurement gap height is then lowered 1000 microns. Sweep occurs from 0.1 to 400 Pa. Data is analyzed via TA Rheology Advantage Data Analysis software.

Yield point is determined at the point at which the oscillatory shear stress begins to deviate from its tangent. The yield point measurements are reported in Pa units.

The linear viscoelastic region (LVR) is the region where the elastic modulus (G') is independent of applied stress. The Average G' is average storage modulus in linear viscoelastic region (LVR) range of dynamic oscillation stress sweep.

Kruss Lather Analyzer (Bubble Size)

The commercially available Kruss lather analyzer DFA100, supplied from Kruss, is used to analyze the foam for the initial Sauter mean radius $R_{32}$ (bubble size). The foam is dispensed into the CY4571 column containing a prism. An internal stopper is placed into the column approximately 100 ml from the top of the chamber. The camera height is set to 244 mm and camera position is placed in the 3 slot. Structure foaming is captured at 2 frames per second for 120 seconds. Data analysis is performed on the Kruss Advance 1.5.1.0 software application version.

Shear Stress

Shear stress is measured by shear rate sweep condition with a rheometer available from TA Instruments with a mode name of ARG2. Geometry has 40 mm diameter, 2° C. cone angle, and gap of 49 µm. Shear rate is logarithmically increased from 0 to 1200/s for 1 min, and temperature is kept at 26.7° C. Share stress at a high shear rate of 950/s is measured and defined above.

EXAMPLES

The composition, orifice shapes, and dispensers illustrated in the following Examples illustrate specific embodiments but are not intended to be limiting thereof. Other modifications can be undertaken by the skilled artisan without departing from the spirit and scope of this invention.

All exemplified amounts are listed as weight percents and exclude minor materials such as diluents, preservatives, color solutions, imagery ingredients, botanicals, and so forth, unless otherwise specified. All percentages are based on weight unless otherwise specified.

TABLE 1

Shampoo Composition

| Ingredient | Wt. % |
|---|---|
| Distilled Water | 55.47 |
| Anionic Surfactant[1] | 22.08 |
| Co-Surfactant[2] | 5.52 |
| Cationic Deposition Polymer[3] | 0.37 |
| Silicone[4] | 1.38 |
| Additional Components[5] | 7.18 |
| Propellant[6] | 8.00 |

[1] Sodium Undecyl Sulfate
[2] Lauramidopropyl Betaine
[3] Guar Hydrohypropyltrimonium Chloride, Jaguar® C-500 from Solvay
[4] Silicone Quaternium-22
[5] Includes one or more viscosity modifiers, pH adjusters, fragrances, dyes, and preservatives.
[6] Trans-1,3,3,3-tetrafluoropropene (HFO 1234ze available by Honeywell®)

The shampoo composition in Table 1 has an elastic modulus of 30.05 Pa and α=0.2. This example and was dispensed through the shaping orifices in Table 2 and Table 3, below.

TABLE 2

Figure 12A:
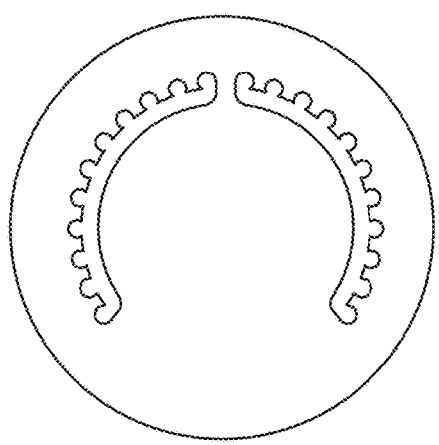
FIG. 12A is the orifice used in Example B.
Figure 12B:
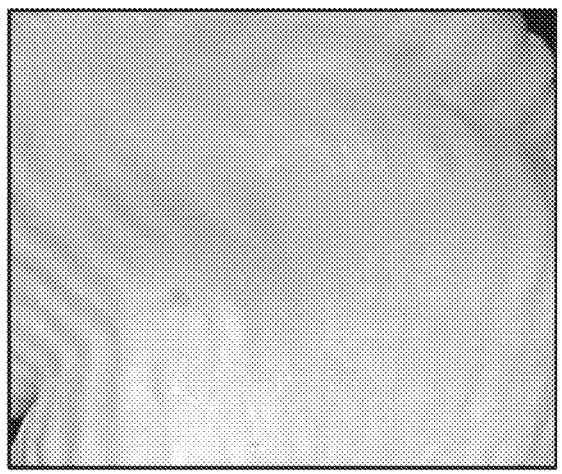
FIG. 12B is a photograph of the foam produced by the orifice in FIG. 12A in Example B.

| | Ex. A | Ex. B | Ex. C | Ex. D | Ex. E |
|---|---|---|---|---|---|
| G' (Pa) | 30.05 | 30.05 | 30.05 | 30.05 | 30.05 |
| Instantaneous foam density (g/cc) | 0.15 | 0.15 | 0.15 | 0.15 | 0.15 |
| Delivery Rate (g/s) | 9.0 | 9.0 | 9.0 | 9.0 | 9.0 |
| Delivery Rate (mL/s) | 60 | 60 | 60 | 60 | 60 |
| Dosage (g) | 5-7 | 5-7 | 5-7 | 5-7 | 5-7 |
| Total Orifice Area, $S_{TOT}$ (mm²) | 95 | 64 | 31 | 26 | 60 |
| Linear Velocity (mm/s) | 631.6 | 938 | 1910 | 2308 | 1000 |
| Shaping Orifice Area, $S_{SH}$ (mm²) | 95 | 64 | 31 | 26 | 60 |
| notches$_{norm}$ | 0.67 | 0.49 | 0.00 | 0.43 | 0.62 |
| Frequency of the Vibration | 0.79 | 1.00 | 0.00 | 0.44 | 0.50 |
| Amplitude of the Vibration | 0.18 | 0.30 | 0.00 | 0.44 | 0.50 |
| Nozzle Aspect Ratio | 0.14 | 0.30 | 0.00 | 0.43 | 0.45 |
| Area of the Corolla (mm²) | 125 | 85 | 94 | 38 | 176.7 |
| Space Factor | 0.24 | 0.25 | 0.67 | 0.32 | 0.66 |
| α | 0.2 | 0.2 | 0.2 | 0.2 | 0.2 |
| Shape Factor | 0.21 | 0.17 | 0.17 | 0.09 | 0.37 |
| Comments | Light Texture | Light Texture | Streams form pattern | Surface too small. Foam waves break. | High imprint. Foam shape from orifice preserved |
| Orifices | See FIG. 11A | See FIG. 12A | See FIG. 13A | See FIG. 14A | See FIG. 15A |
| Image of Foam | See FIG. 11B | See FIG. 12B | See FIG. 13B | See FIG. 14B | See FIG. 15B |
| Consumer Perception Mean ± SEM [1-5] | 2.8 ± 0.17 | 2.8 ± 0.17 | 3.0 ± 0.18 | 2.0 ± 0.13 | 4.0 ± 0.15 |

TABLE 3

| | Ex. F | Ex. G | Ex. H | Ex. I | Ex. J |
|---|---|---|---|---|---|
| G' (Pa) | 30.05 | 30.05 | 30.05 | 30.05 | 30.05 |
| Instantaneous foam density (g/cc) | 0.15 | 0.15 | 0.15 | 0.15 | 0.15 |
| Delivery Rate (g/s) | 9.0 | 9.0 | 9.0 | 9.0 | 5.25 |
| Delivery Rate (ml/s) | 60 | 60 | 60 | 60 | 35 |
| Dosage (g) | 5-7 | 5-7 | 5-7 | 5-7 | 5-7 |
| Total Orifice Area, $S_{TOT}$ (mm²) | 25 | 35 | 26 | 3.1 | 18.0 |
| Linear Velocity (mm/s) | 2400 | 1714 | 2341 | 19,099 | 1944 |
| Shaping Orifice Area, $S_{SH}$ (mm²) | 25 | 35 | 26 | 3.1 | 18.0 |
| notches$_{norm}$ | 0.00 | 0.00 | 0.62 | 0.00 | 0.00 |
| Frequency of the Vibration | 0.00 | 0.00 | 0.62 | 0.00 | 0.00 |
| Amplitude of the Vibration | 0.00 | 0.00 | 0.21 | 0.00 | 0.00 |
| Nozzle Aspect Ratio | 0.00 | 0.00 | 0.19 | 0.00 | 0.00 |
| Area of the Corolla (mm²) | 50 | 126 | 38.5 | 3.1 | 18.0 |
| Space Factor | 0.50 | 0.72 | 0.33 | 0.00 | 0.00 |
| α | 0.2 | 0.2 | 0.2 | 0.2 | 0.2 |
| Shape Factor | 0.10 | 0.20 | 0.08 | 0.00 | 0.00 |
| Comments | Foam too weak to hold shape. Loose texture coming out of the orifice. | Streams form pattern. Imprint preserved | Foam too weak to hold shape | No shape/texture | No shape/texture |
| Orifice | See FIG. 16A | See FIG. 17A | See FIG. 18A | See FIG. 19A | See FIG. 20A |
| Image of Foam | See FIG. 16B | See FIG. 17B | See FIG. 18B | See FIG. 19B | See FIG. 20B |
| Consumer Perception of Foam Texture Mean ± SEM [1-5] | 1.4 ± 0.11 | 3.2 ± 0.19 | 1.2 ± 0.08 | 1.5 ± 0.11 | 1.5 ± 0.11 |

Table 2 and Table 3 shows the mean consumer perception along with other characteristics of the orifices and foam.

The consumer perception of the foam texture was determined by showing 30 panelists photographs of the foam in FIGS. 11B to 20B and asking them to give it a ranking based on the following 1-5 scale:
1=no texture
2=some/small level of texture
3=moderate level of texture
4=high level of texture
5=very high level of texture Examples with a mean consumer perception of greater than 2.5 had the most texture and were most preferred by consumers. The foams of Examples A (FIG. 11B), B (FIG. 12B), C (FIG. 13B), E (FIG. 15B), and G (FIG. 17B) had the highest mean consumer perception score and therefore had foam where the texture was visible to consumers. The orifices in these examples had a shape factor from 0.17 to 0.37, an area from 31 to 95 mm$^2$, a corolla area from 85 to 176.7 mm$^2$, and the linear velocity was from 63 to 1910 mm/s.

Examples C (FIG. 13B) and G (FIG. 17B) have a plurality of spaced orifices with a relatively high Space Factor (0.67 and 0.72, respectively). The large Space Factor allows the foam to be dispensed at a relatively high linear velocity (1910 and 1714 mm/s, respectively) while still maintaining a relatively distinct, uniform texture.

Examples A (FIG. 11B) and B (FIG. 12B) also have more than one orifice. However, the Space Factor is lower, as compared to Examples C and G. This can indicate that the orifices are spaced closer together than Examples C and G. However, the orifices in Examples A and B have a larger area, as compared to C and G and the linear velocity is still acceptably fast, but slower than examples C and G. Examples A and B still have a definite texture, however, the texture is lighter and closer together, as compared to the other examples with a mean consumer perception of greater than 2.5.

In Example A (FIG. 11A), the shaping head has a plurality of orifices, in this example 19 orifices, are arranged in an arc on the surface of the shaping head. In this example, the orifices are pin shaped with a circular head and a triangular shaft. The orifices can be from about 0.2 to about 0.8 mm apart, at the closest distance. In this example, the vertices of the triangular shaft are directed towards the center of the shaping head. The heads can be directed towards the periphery of the shaping head and can be located closer to the periphery than the end of the shaft. The diameter of the head can be from about 0.5 to about 1.5 mm and alternatively from about 0.5 to about 1 mm. The shaft has a height from about 3 mm to about 7 mm, alternatively from about 4 mm to about 6 mm, and alternatively about 5 mm. The total surface area of the orifice holds is from about 20 to about 150 mm$^2$, alternatively from about 60 to about 130 mm$^2$, and alternatively from about 80 to about 120 mm$^2$, and alternatively about 100 mm$^2$. Other examples can include a head that can be oval and/or the shaft is a parallelogram/rectangle.

In Example B (FIG. 12A), the shaping head has two orifices in an arc configuration. In another example, the shaping head can have four orifices in a ring configuration. The orifices have a grooved/saw edge pattern on one side and in these examples the pattern is directed towards the outer edge of the shaping head. The opposite side of the orifice can have a smooth edge, directed towards the center of the shaping head. Each groove can have a height (measured from the inner edge to the top of the peak in the saw edge pattern) from about 0.5 to about 1.5 mm, alternatively from about 0.5 to about 1 mm, and alternatively about 1 mm. The distance from peak to peak in the sawtooth pattern can be from about 0.5 to about 1 mm. The surface area of the orifices can be from about 15 to about 80 mm$^2$, alternatively from about 30 to about 65 mm$^2$. The orifices can be located about 1 to about 3 mm from each other, at the closest point.

The shaping orifice Example G (FIG. 17A) has seven orifices in an arc configuration. The orifices are all in the same size and shape. The orifices can be shaped as slits/isosceles triangles with a narrow base as compared to the sides where the base can be directed towards the center of the shaping head and the vertex can be directed towards the outside. The orifices are located at least 1 mm apart.

Example E had highest mean consumer perception and FIG. 15B shows a high imprint with deep groves. Interestingly, Example E has a single shaping orifice shaped like a six-pointed star. Example E was able to achieve this high consumer perception of texture because it has a relatively high nozzle aspect ratio.

Examples D (FIG. 14B), F (FIG. 16B), H (FIG. 18B), I (FIG. 19B), and J (FIG. 20B) had the lowest mean consumer perception score. The orifices in these examples had a lower shape factor (0-0.8), as compared to the higher rated examples, discussed above. These examples also had a smaller area (3.1-26 mm$^2$) and smaller S envelope (3.1-38.5 mm$^2$), as compared to the higher rated examples. The linear velocity of these examples was higher (1944-19,099 mm/s), as compared to the higher rated examples.

Example D (FIG. 14B) and F (FIG. 16B) had a low score because the foam wave breaks, and the pattern is irregular. Example D and E both had relatively small shaping orifice areas (26 and 25 mm$^2$, respectively) resulting in a relatively high linear velocity (2308 mm/s and 2400 mm/s, respectively).

Interestingly, both the orifices in examples C (FIG. 13A) and F (FIG. 16A) have a shaping orifice that comprises a plurality of round holes spaced evenly apart in a ring. However, Example C produces a shaped foam with a high average consumer perception score (3.0±0.18) and Example F produced a low average consumer perception score (1.4±0.11). The space factor and area are lower in Example F, resulting in a higher linear velocity and causing a foam to dispense with a relatively low level of texture.

Figure 13A:
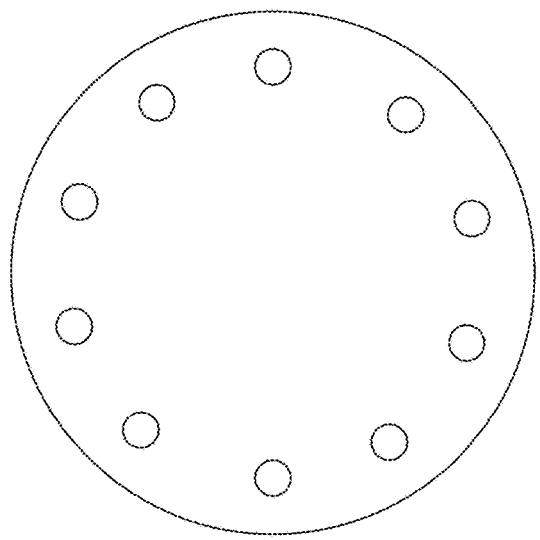
FIG. 13A is the orifice used in Example C.
Figure 13B:
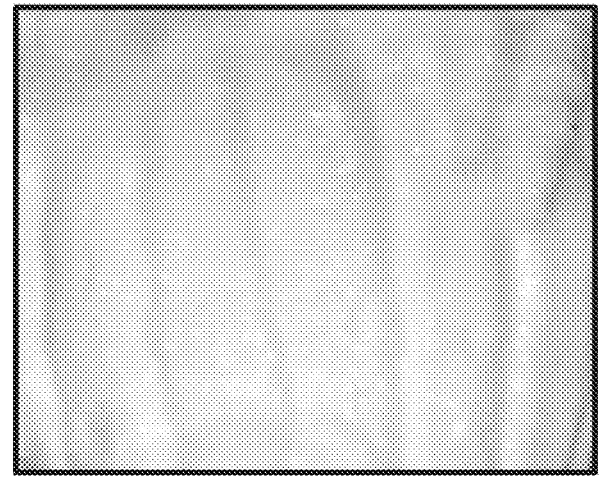
FIG. 13B is a photograph of the foam produced by the orifice in FIG. 13A in Example C.
Figure 14A:
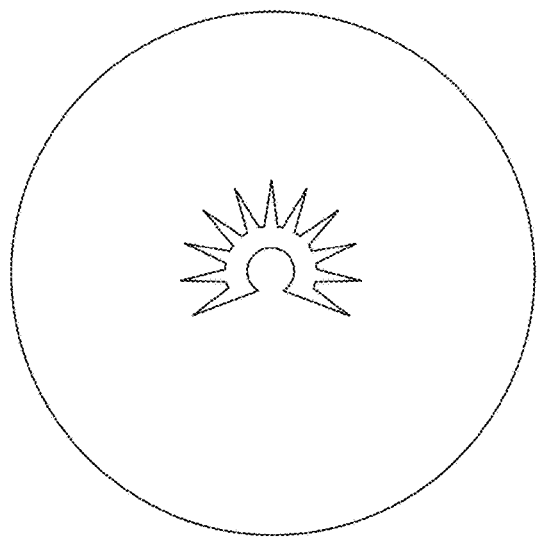
FIG. 14A is the orifice used in Example D.
Figure 14B:
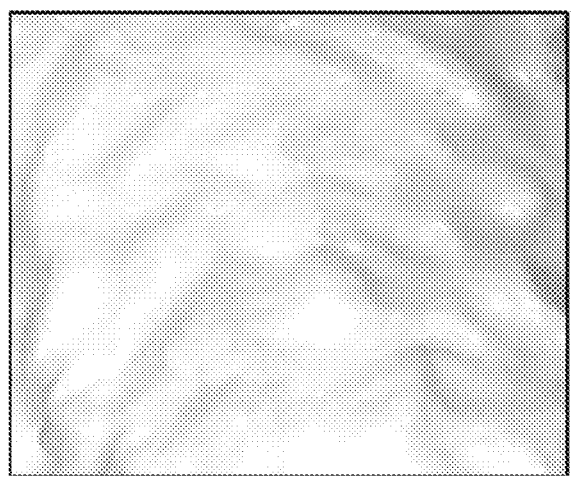
FIG. 14B is a photograph of the foam produced by the orifice in FIG. 14A in Example D.

In FIG. 13A, the shaping head has ten orifices in a ring configuration with the orifices spaced about 1 mm apart. In FIG. 16A, the shaping head has eight orifices in a ring configuration with the orifices spaced about 1 mm apart. In FIGS. 13A and 16A, the orifices are all in contact with the external convex hull.

Example H had the lowest mean consumer perception and the foam appears irregular and random. Example H is a star shape, like Example E. However, the different shapes of the two stars result in a smaller area, nozzle aspect ratios, and space factor for Example H, as compared to Example E. The linear velocity of Example H is over twice the linear velocity of Example H.

Examples I and J also had low mean consumer perception and the foam appears like a smooth blob. Both examples have a shape factor of 0 and a single shaping orifice. The shaping orifice in Example I is round and has a small area, 3.1 mm$^2$, which caused a relatively high linear velocity. The shaping orifice in Example J is an oval and has a relatively low area and high linear velocity.

Combinations

A. A method of dispensing a textured foam from an aerosol container comprising:
  a. providing an aerosol foam dispenser comprising:
    i. a pressurizable outer container for storing a propellant and a composition under pressure;
    ii. an actuator where the actuator is attached to a top of the outer container comprising:
      1. a valve being movable to an open position to release a mixture of the aerosol and the composition;
      2. a trigger for actuating the valve;
      3. a nozzle comprising a nozzle surface comprising one or more shaping orifices;

wherein said orifices are in fluid communication with the valve;
b. actuating the trigger;
c. dispensing a foam composition at a linear velocity; wherein the foam composition comprises an elastic modulus from about 10 Pa to about 200 Pa; wherein the method comprises a shape factor from about 0.11 to about 1.

B. The method according to Paragraph A, wherein the shape factor is from about 0.12 to about 0.75, preferably from about 0.13 to about 0.5, more preferably from about 0.15 to about 0.45, more preferably from about 0.16 to about 0.40, even more preferably from about 0.17 to about 0.37, and most preferably from about 0.20 to about 0.37.

C. The method according to Paragraphs A-B, wherein the foam comprises an a from about 0.1 to about 0.6.

D. The method according to Paragraphs A-C, wherein the linear velocity comprises from about 0.5 m/s to about 2.4 m/s, preferably from about 0.5 m/s to about 1.94 m/s, more preferably from about 0.6 m/s to about 1.925 m/s, more preferably 0.631 mm/s to about 1.910 m/s, and even more preferably from about 1.0 m/s to about 1.714 m/s.

E. The method according to Paragraphs A-D, wherein the foam comprises an elastic modulus from about 15 to about 175 Pa, preferably from about 20 to about 150 Pa, preferably from about 25 to about 125 Pa, and more preferably from about 30 to about 100 Pa.

F. The method according to Paragraphs A-E, wherein the foam comprises a stiffness value from about 0.1 to about 0.6, preferably from about 0.15 to about 0.5, and more preferably from about 0.2 to about 0.4.

G. The method according to Paragraphs A-F, wherein the foam comprises an instantaneous foam density from about 0.01 g/mL to about to about 0.4 g/mL, preferably from about 0.03 to about 0.3 g/mL, more preferably from about 0.05 g/mL to about 0.25 g/mL, and most preferably from about 0.07 g/mL to about 0.2 g/mL.

H. The method according to Paragraphs A-G, wherein the composition comprises a shampoo composition comprising one or more surfactants, an aqueous carrier, and optionally a cationic deposition polymer.

I. The method according to Paragraphs A-H, wherein the composition comprises a conditioner composition comprising a cationic surfactant, a high melting point fatty compound, an aqueous carrier, and optionally a silicone.

J. An aerosol foam dispenser comprising:
a. a pressurizable outer container for storing a propellant and a composition under pressure;
b. an actuator where the actuator is attached to a top of the outer container comprising:
  i. a valve being movable to an open position to release a mixture of the aerosol and the composition;
  ii. a trigger for actuating the valve;
  iii. a nozzle comprising a nozzle surface comprising one or more shaping orifices;
  wherein the nozzle surface comprises a space factor greater than 0.5.

K. The aerosol foam dispenser according to Paragraph J wherein the nozzle surface comprises a nozzle aspect ratio greater than 0 and less than 0.5 and preferably from about 0 to about 0.45.

L. The aerosol foam dispenser according to Paragraphs J-K, wherein the nozzle surface comprises one shaping orifice comprising a $notches_{norm}$ greater than 0, preferably from about 0 to about 0.75, more preferably from about 0 to about 0.7, and most preferably from about 0 to about 0.67.

M. The aerosol foam dispenser according to Paragraphs J-L, wherein the one or more shaping orifice comprise an area from about 27 mm$^2$ to about 120 mm$^2$, preferably from about 29 mm$^2$ to about 110 mm$^2$, more preferably from about 31 mm$^2$ to about 95 mm$^2$, and even more preferably from about 35 mm$^2$ to about 60 mm$^2$.

N. The aerosol foam dispenser according to Paragraphs J-M, wherein the nozzle surface comprises more than one shaping orifice comprising a total shaping orifice area of greater than 60 mm$^2$.

O. The aerosol foam dispenser according to Paragraphs J-O wherein the nozzle surface comprises a corolla and the area of the corolla is from about 51 mm$^2$ to about 225 mm$^2$, preferably from about 70 mm$^2$ to about 190 mm$^2$, more preferably from about 85 mm$^2$ to about 177 mm$^2$, and even more preferably from about 125 mm$^2$ to about 177 mm$^2$.

P. The aerosol foam dispenser according to Paragraphs J-O, wherein the nozzle surface does not comprise a central orifice.

Q. The aerosol foam dispenser according to Paragraphs J-P, wherein the dispenser is selected from the group consisting of dip tube, barrier aerosols, and combinations thereof.

R. The aerosol foam dispenser according to Paragraphs J-Q, wherein the dispenser is a dip tube where an end of the dip tube is connected to the valve.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of dispensing a textured foam from an aerosol container comprising:
   a. providing an aerosol foam dispenser comprising:
      i. a pressurizable outer container for storing a propellant and a composition under pressure;
      ii. an actuator where the actuator is attached to a top of the outer container comprising:
         1. a valve being movable to an open position to release a mixture of the aerosol and the composition;
         2. a trigger for actuating the valve;
         3. a nozzle comprising a nozzle surface comprising one or more shaping orifices;
            wherein said orifices are in fluid communication with the valve;
   b. actuating the trigger;
   c. dispensing a foam composition at a linear velocity;
      wherein the foam composition comprises an elastic modulus from about 10 Pa to about 200 Pa;
      wherein the method comprises a shape factor from about 0.11 to about 1.

2. The method of claim 1 wherein the shape factor is from about 0.12 to about 0.75.

3. The method of claim 1 wherein the foam comprises an α from about 0.1 to about 0.6.

4. The method of claim 1 wherein the linear velocity is from about 550 m/s to about 1935 m/s.

5. The method of claim 1 wherein the foam comprises an elastic modulus from about 15 to about 175 Pa.

6. The method of claim 1 wherein the foam comprises a stiffness value from about 0.1 to about 0.6.

7. The method of claim 1 wherein the foam comprises an instantaneous foam density from about 0.01 g/mL to about to about 0.4 g/mL.

8. The method of claim 1 wherein the composition comprises a shampoo composition comprising one or more surfactants, an aqueous carrier, and optionally a cationic deposition polymer.

9. The method of claim 1 wherein the composition comprises a conditioner composition comprising a cationic surfactant, a high melting point fatty compound, an aqueous carrier, and optionally a silicone.

10. An aerosol foam dispenser comprising:
    a. a pressurizable outer container for storing a propellant and a composition under pressure;
    b. an actuator where the actuator is attached to a top of the outer container comprising:
       i. a valve being movable to an open position to release a mixture of the aerosol and the composition;
       ii. a trigger for actuating the valve;
       iii. a nozzle comprising a nozzle surface comprising one or more shaping orifices;
           wherein said orifices are in fluid communication with the valve;
           wherein the nozzle surface comprises a space factor greater than 0.5.

11. The aerosol foam dispenser of claim 10 wherein the nozzle surface comprises a nozzle aspect ratio from about 0 to about 0.45.

12. The aerosol foam dispenser of claim 10 wherein the nozzle surface comprises a nozzle aspect ratio greater than 0 and less than 0.5.

13. The aerosol foam dispenser of claim 10 wherein the nozzle surface comprises one shaping orifice comprising a $notches_{norm}$ greater than 0.

14. The aerosol foam dispenser of claim 13 wherein the shaping orifice comprises an area greater than 30 mm$^2$.

15. The aerosol foam dispenser of claim 10 wherein the nozzle surface comprises more than one shaping orifice comprising a total shaping orifice area of greater than 60 mm$^2$.

16. The aerosol foam dispenser of claim 10 wherein the nozzle surface comprises a corolla and the area of the corolla is greater than 50 mm$^2$.

17. The aerosol foam dispenser of claim 10 wherein the nozzle surface does not comprise a central orifice.

18. The aerosol foam dispenser of claim 10 wherein the dispenser is selected from the group consisting of dip tube, barrier aerosols, and combinations thereof.

19. The aerosol foam dispenser of claim 18 wherein the dispenser is a dip tube where an end of the dip tube is connected to the valve.

* * * * *